United States Patent [19]

Steers et al.

[11] Patent Number: 5,698,549
[45] Date of Patent: Dec. 16, 1997

[54] METHOD OF TREATING HYPERACTIVE VOIDING WITH CALCIUM CHANNEL BLOCKERS

[75] Inventors: William D. Steers, Charlottesville; Jeremy B. Tuttle, Earlysville, both of Va.

[73] Assignee: UVA Patent Foundation, Charlottesville, Va.

[21] Appl. No.: 474,979

[22] Filed: Jun. 7, 1995

Related U.S. Application Data

[63] Continuation-in-part of Ser. No. 241,776, May 12, 1994, Pat. No. 5,503,986.

[51] Int. Cl.⁶ .......................... A61K 31/55; A61K 31/135
[52] U.S. Cl. ............................................. 514/211; 514/654
[58] Field of Search .................................... 514/211, 654

[56] References Cited

U.S. PATENT DOCUMENTS 5,252,337 10/1993 Powell ..................................... 424/456
5,354,765 10/1994 Pang et al. ............................. 514/356

OTHER PUBLICATIONS

Isselbacher, K.J. et al. Harrison's Principles of Internal Medicine, New York: McGraw-Hill, 1985, p. 1353.

Lodish, H et al. Molecular Cell Biology. New York: Scientific American Books, 1986.

Thomas, C.L. Taber's Cyclopedic Medical Dictonary F.A. Davis Co., 1985, p. 1123.

Chodak, G.W., et al. "Increased levels of Fibroblast Growth. Factor–like Activity in Urine from Patients with Bladder or Kidney Cancer." Cancer Research 48:2083–2088, 1988.

Morrison, R.S. "Fibroblast Growth Factors: Potential Neutrophic Agents in the Central Nervous System." Journal of Neuorscience Research 17:99–101, 1987.

"Nerve Growth Factor in the Urinary Bladder of the Adult Regulates Neuronal Form and Function", W.D Steers et al, Journal for Clinical Investigations, vol. 88, Nov. 1991, pp. 1709–1715.

"Nerve Growth Factor Responsiveness of Cultured Major Pelvic Ganglion Neurons from the Adult Rat", Jeremy B. Tuttle et al, Brain Research, 588 (1992) 29–40.

Calcium Channel Antagonists Prevent Urinary Bladder Growth and Neuroplasticity Following Mechanical Stress, William D. Steers et al, American Journal of Physiology, 1994, pp. 20–26.

*Primary Examiner*—William R.A. Jarvis
*Attorney, Agent, or Firm*—Sheldon H. Parker

[57] ABSTRACT

The instant invention discloses a method of treating hyperactive voiding associated with excessive nerve growth factor production and nerve growth in patients by administering a $Ca^{++}$ channel blocker. The $Ca^{++}$ channel blockers verapamil and diltiazem can be administered systemically to treat hyperactive voiding, such as is associated with benign prostatic hyperplasia and interstitial cystitis.

6 Claims, 13 Drawing Sheets

METHOD OF TREATING HYPERACTIVE VOIDING WITH CALCIUM CHANNEL BLOCKERS

CROSS REFERENCE TO RELATED APPLICATIONS

This is a continuation-in-part of application Ser. No. 08/241,776 filed on May 12, 1994, now U.S. Pat. No. 5,503,986.

BACKGROUND OF THE INVENTION

1. Field of the Invention

The invention relates to the use of $Ca^{++}$-channel blockers is disclosed to inhibit the production of NGF and nerve growth. Additionally, the isolation of markers in urine to indicate the presence of irritative and/or obstructive conditions in the bladder.

2. Brief Description of the Prior Art

Historically, there has been a progression from anatomical to functional studies for the diagnosis of upper and lower urinary tract obstruction. However, these studies fail to predict ultimate changes in bladder or kidney function. For example, with obstruction of the lower urinary tract, urodynamic studies often do not correlate with the severity of symptoms and fail to demonstrate capacity for return to normal function following relief of obstruction.

Two major classes of voiding disorder in males and females are benign prostatic hyperplasia (BPH) and interstitial cystitis (IC). These cause, respectively, irritative/obstructive symptomology and idiopathic bladder and pelvic pain with voiding. An accumulating body of information links these conditions to changes in bladder innervation and that these may be orchestrated by neurotrophic factors.

Interstitial cystitis (IC) is an enigmatic disorder associated with chronic inflammation, whose primary manifestations are bladder pain and irritative voiding. IC affects up to 90,000 individuals and may be a heterogeneous syndrome yet therapy for this disease is inadequate. Since IC does not lead to life threatening problems such as renal insufficiency, infection or hemorrhage, a reasonable approach to therapy is to alleviate symptoms. However, lack of knowledge of the underlying pathophysiological cause(s) for this disorder has hampered the design of rational interventions. Because the cardinal symptoms of IC are bladder pain, urinary urgency or frequency not associated with involuntary bladder contractions, it can be assumed that activation of nociceptive afferents and/or pathways occur in IC. Nociceptive (pain) afferents and pathways are the specific and separate neural substrates for pain. Thus, a chronic pain disorder implies an alteration in the function of the nociceptive system.

Research on IC has been primarily focused on immunologic processes and urothelial permeability. However, inflammatory mediators and other second messengers alter bladder nerve activity and change production of growth factors including those trophic for nerves. Products released by inflammatory cells such as mast cells and lymphocytes, or alterations in urothelial permeability, may result in structural and functional changes in the bladder afferents and sensory pathways, including the nociceptive elements. There is no non-invasive diagnostic test available to determine whether a patient has IC.

Benign prostatic hyperplasia (BPH) is a disease in men characterized histologically by the formation of non-malignant prostatic nodules, and clinically by signs and symptoms of urinary obstruction produced by this abnormal growth. BPH accounts for an estimated 1.7 million physician office visits and nearly 400,000 prostatectomies in the United States and is the most common cause of major surgery in men over age 55. Despite the high prevalence and social impact of BPH, very little is known regarding the pathogenesis of symptoms accompanying outlet obstruction of the bladder. This is especially relevant since symptoms and subjective clinical findings are the primary indications for intervention in BPH. Irritative symptoms, including urinary urgency, frequency and nocturia, are closely correlated with the need for intervention and have the greatest negative impact on the patients' quality of life. Additionally, BPH can cause an infravesical obstruction, and consequent damage to the detrusor muscle, even in the absence of troublesome symptoms and without a demonstrably enlarged prostate gland. Conversely, BPH, even with significant prostatic enlargement, does not always result in functionally obstructed voiding.

The degree of BPH has been assessed by estimating prostate size on a digital rectal exam. However, the degree of obstruction is not correlated with prostate size, probably due in part to location and the minimal involvement of the whole gland in infravesical obstruction. This indicates overall prostate size alone has poor sensitivity and specificity for the important symptoms of BPH.

Combined pressure/flow studies have been used to document obstruction of the bladder but this invasive test is expensive and requires special expertise and thus is a poor routine screening tool. A voiding flow rate offers a less invasive method of inferring obstruction, but this also suffers from poor specificity and sensitivity for obstruction. Despite these limitations, flow rate is used in the diagnosis, management and outcome analysis of BPH. Recently, a symptom index has been developed for BPH capable of discriminating between BPH and control subjects. This AUA International Prostate Symptom Score (I-PSS) has been shown to be internally consistent and to have excellent test-retest reliability. This self-administered questionnaire serves as an established and validated means of capturing the symptom severity of BPH. Questionnaire features and its performance suggest it is useful for discriminative, predictive and evaluative purposes. The I-PSS is not recommended to screen for BPH, but rather to assess symptom severity. The I-PSS may also be useful, with minor modification, for measuring severity of symptoms of other lower urinary tract disorders such as interstitial cystitis.

Further insight into the functional and structural consequences that accompany BPH has been obtained via transabdominal ultrasound of the bladder. This imaging method has been used to measure residual urine volume, estimate bladder wall thickness, indicate the extent of trabeculation and to help exclude other pathologies such as hydronephrosis, tumor and bladder stones in a minimally invasive manner.

In addition to IC and BPH, pain or discomfort is produced by other causes of bladder inflammation which include bacterial and parasitic infections, calculi, foreign bodies such as catheters, trauma, neoplasm, radiation therapy and chemotherapy. Some middle aged women suffer from an irritative voiding disease similar to BPH in men. Patients with inflammatory disorders often report that symptoms are affected by dietary substances, suggesting a direct effect of bladder contents on nerve activity or a functional alteration in afferents. IC patients report that the disease has a very uneven clinical course. Periods of intense pain and irritative voiding are interspersed with extended periods of time of relative freedom from symptoms. However, efforts to detect specific substances in the urine that reflect active or inactive phases of the disease, or that have diagnostic utility, have not met with success. No useful, protective or palliative dietary regimen has been discovered.

A diagnostic test would be useful to indicate for whom intervention is necessary and effective before irreversible end organ damage occurs. A reasonable approach would be to identify molecular messengers produced by the kidney and/or bladder in response to mechanical stress, inflammatory processes or other causes, such as age, which dictate subsequent functional change in smooth muscle cells or neurons to be used as biochemical markers for future dysfunction.

The bladder innervation is composed of sensory elements from the dorsal root ganglia (DRG afferents), reflex connections in the central nervous system, and the parasympathetic and sympathetic ganglion neurons that regulate bladder filling and emptying. These neurons require neurotrophic factors for the maintenance of normal function, and peripheral neurons such as those innervating the bladder often acquire the factors from innervated tissues. Noradrenergic sympathetic neurons and many of the DRG sensory afferent neurons respond to the best-known neurotrophin: nerve growth factor (NGF). NGF is a member of a family of related neurotrophins that share structural similarities, a family currently known to include brain-derived neuronotrophic factor (BDNF), NT-3 and NT-4/5. These neurotrophins demonstrate overlapping specificities in bioassays and can interact with more than a single high-affinity binding site. Parasympathetic neurons do not require NGF but certain populations respond to other signaling proteins, such as ciliary neuronotrophic factor (CNTF) or basic fibroblastic growth factor (bFGF). Many of the details of neurotrophic factor biodynamics are not well known, especially in mixed neuronal populations and in adult organisms, and participation in disease remains a distinct but largely unknown possibility. Whether neurotrophic factors regulate adult neural plasticity is also a largely open question. There is no reason to expect that these large protein molecules (ca. 26 kDa) would appear in the urine either normally or as the result of a disease process. The proteins are cell-cell signals used for regulation of growth and function and not at all similar to hormones that circulate systemically.

BRIEF DESCRIPTION OF THE DRAWINGS

The advantages of the instant disclosure will become more apparent when read with the specification and the drawings, wherein.

SUMMARY OF THE INVENTION

Figure 1:
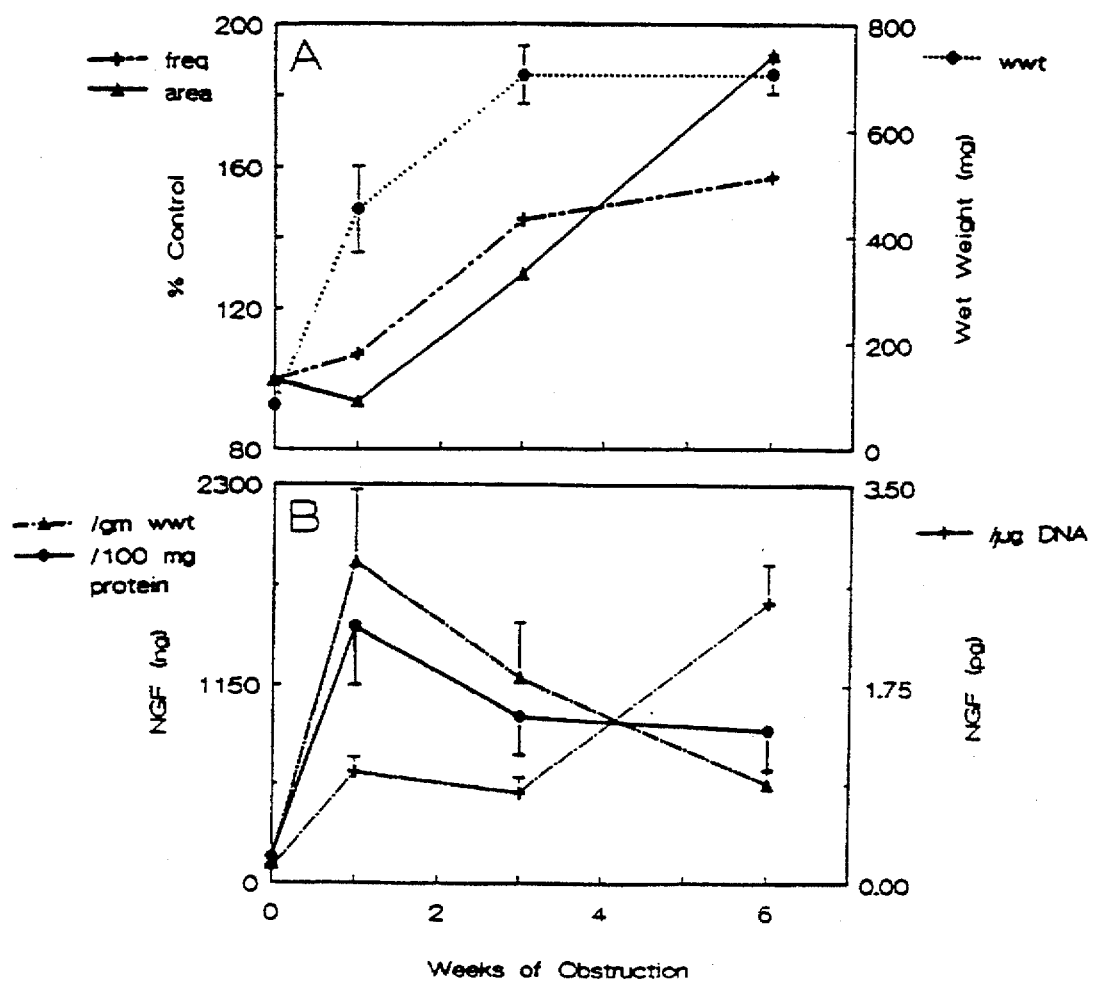
FIG. 1A is a graph illustrating time course of changes in bladder weight over a seven day period following experimental partial outlet obstruction.
FIG. 1B graphs NGF tissue levels over the same time period as FIG. 1A.

The instant invention discloses a method of inhibiting nerve growth factor production and nerve growth associated with neuroplasticity. The production, and subsequently growth, is inhibited by administering a $Ca^{++}$ channel blocker, such as verapamil or diltiazem. Neuroplasticity is associated with hyperactive voiding and hypertension. The $Ca^{++}$ channel blockers are administered systemically.

The instant invention further discloses a method of detecting lower urinary tract disease from a urine sample by determining the concentration of a neurotrophic factor. The concentration of the neurotrophic factor is compared to a normal concentration. The preferred neurotrophic factor is nerve growth factor, which has a normal concentration of approximately less than 8 picogram per milliliter. The concentration of the nerve growth factor in the urine generally rises at the onset of lower urinary tract disease and decreases as the disease progresses.

DETAILED DESCRIPTION OF THE INVENTION

A focus on symptoms and lack of basic information on symptom pathogenesis has generated complex problems regarding treatment effectiveness and treatment modality of irritative voiding. It is known that hypertrophied bladders of rat and human contain significantly more NGF per milligram wet weight, protein and DNA than normal bladders. Steers, W. D., Kolbeck, S., Creedon, D and Tuttle, J. B., *Nerve Growth Factor in the Urinary Bladder of the Adult Regulates neuronal Form and Function*, Journal for Clinical Investigations, Vol. 88, November 1991. Obtaining tissue samples, however is an invasive procedure. A non-invasive marker for the analysis of increased NGF in association with voiding disorders would allow for a rapid, inexpensive method of indicating a disorder. The research originated from the hypothesis that if NGF were being produced in the bladder and produced in excess as the result of disease processes, and if urine were stored in the bladder for a significant amount of time, and if the NGF protein somehow made its' way into the urine and if the NGF were not degraded into peptide fragments, and if the NGF reached sufficiently high concentration to be measured by present methods, then perhaps NGF or similar protein signals could serve as a non-invasive urine marker for significant lower urinary tract disease. It has now been found that NGF does, in fact, serve as a non-invasive urinary tract marker.

Considerable debate has surrounded the issue of success in men treated for BPH without objective markers that measure outcome. It would be useful to discover a urinary marker capable of shedding light on symptom pathogenesis or which could be used to monitor the development, severity or resolution of symptoms. A marker that is capable of predicting the success of various treatment options would have significant value and offer important cost savings. Beyond this, obstruction and detrusor hypocontractility with BPH often result in residual urine and obstructive voiding symptoms, in addition to irritative symptoms. A urinary marker correlated with hyper- or hypoactivity would carry further utility in these cases.

Data suggests that growth factors and certain second messengers, such as protein kinase C, regulate cellular responses to mechanical stress including hypertrophy. These second messengers are responsible for eventual end organ disease. It is possible that up-regulation of these factors can be detected before alterations occur in target tissues. It is disclosed that myotrophic and neurotrophic growth peptides are released into the urine or blood in response to mechanical stress. The myotrophic and neurotrophic substance of basic fibroblast growth factor (bFGF) present in the urine of some men with BPH or prostate cancer indicates that such growth factors can be measured and correlated to the degree of obstruction and patient symptoms. Testing data in animals has shown that partial urethral ligation is associated with high levels of NGF, only in the urinary bladder, not in most other tissues tested. One distinct site, the spleen, also had elevated levels of NGF after bladder outlet obstruction. The increase in NGF in the bladder of obstructed animals has been correlated in the alterations in the form and function of bladder neurons which in turn has been linked to hyperactive voiding. NGF levels rise more than a week prior to hyperactive voiding, thereby indicating that tissue levels of this neurotrophic factor can rise with mechanical obstruction and are linked with voiding dysfunction. In certain neuropathic conditions, such as neuropathy due to herpes simplex, an increase in nerve growth factor in the serum has been measured.

The extensive tissue changes that occur in the bladder are reflected by the disclosed molecular neurotrophic markers in the urine, which allow for the development of novel diagnostic tests and new therapies for these diseases. The uncertain nature of medical and surgical treatments for BPH and IC can be clarified by the disclosed Urine markers that relate to symptoms, severity or is predictive of future disease progression. By analogy, serum enzyme tests are used to indicate myocardial damage and the measurement of serum PSA to indicate prostatic disease.

Neurotrophic factors such as nerve growth factor (NGF) and basic fibroblastic growth factor (bFGF) regulate the form and function of neurons in the micturition pathways. Voiding dysfunctions observed with benign prostatic hyperplasia (BPH) and interstitial cystitis (IC) involve significant alterations in afferent signaling from the bladder. Afferent remodeling is driven by changes in neurotrophic factor production by the bladder. Relief of obstruction is followed by a reversal of these neuronal changes and a decrease in neurotrophic factors. Urine levels of NGF and bFGF reflect production of these factors in the bladder and subsequent pathophysiological processes associated with disturbances in voiding, thereby predicting treatment outcome. Levels, pattern or presence of NGF additionally indicate the progress of disease. Levels of NGF rise with the onset of disease and, as the body settles into the disease, NGF levels drop. By monitoring NGF, the future potential includes classifying diseases into groups for treatment and determining whether patients require surgery or medication for treatment.

NGF and bFGF have been measured by two-site ELISA in the urine of patients with BPH, prostate cancer, IC and in experimental animals with bladder outlet obstruction and bladder inflammation. Urine neurotrophin levels can provide clinicians with a predictor of optimal treatment in men with symptomatic BPH and women with IC or irritative voiding symptoms.

While there are many consequences unique to IC or BPH, the two diseases share heuristic parallels. Both are characterized by altered voiding patterns, an incomplete understanding of the pathogenesis and a focus on patients' subjective symptoms for diagnosis and treatment. BPH and IC often involve irritative discomfort and result in bladder dysfunction. The treatments available for IC and BPH often fail to relieve the irritative voiding symptoms (BPH) or do so only temporarily (IC). Understanding and treatment of both are significantly advanced by the disclosed non-invasive urine test, thus reducing health care costs and improving the quality of care.

Remodeling of sensory pathways occurs in patients with IC and immunohistochemical data reveals that patients with IC have more nerves in the submucosa and muscle of the bladder. Chemically induced bladder inflammation in animals has been shown to reduce the threshold of mechanoreceptive afferents, and to alter the micturition reflex. Current therapy for IC is directed at interruption of afferent transmission from the bladder using intravesical anesthetics such as lidocaine and DMSO, electrical stimulation of sacral nerve roots, or denervation by cystolysis, hydrodistension or sacral rhizotomy. These therapies have partial and often only temporary success. Insight into the possible explanation for the failure of the therapies derives from the experience of patients undergoing radical cystectomy or partial cystectomy with bladder augmentation. Even in these cases, surgical removal of the bladder does not uniformly abolish the sensation of bladder pain. This phenomenon is similar to the phantom limbs experienced by patients after amputation of an extremity. These findings suggest that mechanisms central to peripheral afferents play a role in chronic dysesthesias and pain. Sensory remodeling of afferent pathways from the urinary bladder occurs in response to obstruction, denervation and diabetes. Therefore it is reasonable to suggest that sensory remodeling could develop in the spinal nociceptive pathways from the bladder in IC, reinforcing and/or reflecting the proliferation of axons in the bladder.

There are several potential mechanisms that could lead to these structural and functional alterations following inflammation. In the rat, pelvic and hypogastric nerves contain peptidergic afferent fibers supplying the bladder. Myelinated A-$\delta$ and unmyelinated C-fiber afferents in the pelvic nerve arise in the $L_6$ and $S_1$ dorsal root ganglia (DRG) while those in the hypogastric nerve are situated in the $L_1$ and $L_2$ DRG. The afferents that trigger micturition are myelinated. It is assumed, but not established, that the unmyelinated fibers are primarily nociceptive since they do not respond to non-painful bladder distension. It is unclear whether myelinated fibers from the bladder contribute to pain sensation. Hypertrophy of $L_6$ and $S_1$ DRG neurons occurs in response to inflammation, obstruction and denervation of bladders in adult rats. The structural alteration is associated with changes in afferent transmission and connectivity within the $L_6$ and $S_1$ spinal cord segments. It is also possible that structural alterations occur in $L_1$ and $L_2$ afferents. Recent evidence strongly suggests that nerve growth factor (NGF) produced by the bladder smooth muscle is responsible for a portion of these structural and functional changes.

Obstruction of the urinary bladder causes smooth muscle hypertrophy, and sometimes hyperplasia with a coexisting increase in bladder collagen. Thus, obstruction caused by growth of the prostate in BPH secondarily causes significant growth and genetic changes in the bladder tissue. Partial urethral ligation in the rat causes similar morphological and histological changes. This increase in bladder size in animals has been associated with profound changes in sensory and motor nerves to the urinary bladder. Alterations in the sensory nerves and the micturition reflex are, in turn, postulated to play a role in irritative voiding symptoms. Therefore, a link between the pathophysiological events surrounding BPH and the symptoms that are the focus of patient concern and treatment evaluation. Evidence indicates neurotrophic signaling proteins, such as NGF and bFGF, are produced by innervated tissues and direct the growth, connectivity and function of visceral neurons. In fact, NGF is necessary for normal development, maintenance and response properties of mechanosensitive afferents. NGF and bFGF are produced in the bladder and are elevated with bladder obstruction. Infravesical obstruction causes the detrusor muscle to enter a synthetic mode which in turn results in changes in the bladder innervation. The growth of detrusor muscle involves excess production of NGF and bFGF, enough for the proteins to be detected in the urine of affected patients and animals. This indicates a growth-associated increase precedes changes in the bladder innervation and presage, or accompany, the onset of irritative voiding symptoms.

NGF and bFGF in the urine arise from sources in the lower urinary tract. They reflect the presence of active growth or inflammation and participate in the etiology of irritative voiding and therefore can be used to predict and/or monitor treatment success. To determine whether the levels of NGF and bFGF in the urine correlate with IC, BPH, obstruction or inflammation testing was done on human and animal subjects.

Following intervention for obstruction, 25–60% of patients continue to experience irritative voiding symptoms. This appears to be especially true of hormonal manipulation which prevents conversion of testosterone to dihydrotestosterone which is required for BPH. Inhibiting 5-α-reductase can reduce prostate size by 30% but have relatively little effect on irritative voiding symptoms when compared to other therapies. Levels of neurotrophins produced by the bladder direct changes in bladder innervation which are linked to sensory symptoms, do not decrease following intervention when sensory symptoms persist. Conversely, if neurotrophins are not elevated in symptomatic patients, therapy may be too late and outcome unaltered. This finding not only provides insight into the cause of persistent symptoms, providing a potential explanation for intervention failure, but strengthens the hypothesis that symptoms are associated with altered bladder innervation. Thus, the population can be segmented into groups likely and less likely to benefit from specific therapy or procedures.

The neurotrophin NGF has been firmly established as critical for the survival, growth and normal maintenance of peripheral sensory neurons. NGF can also function as a retrograde messenger between a peripheral target and its innervation. Since axonal processes are increased in the bladders of patients with IC, and possibly chronic bacterial cystitis, some alteration occurs in the bladder tissue to lead to increased nerve infiltration. The size of DRG cells projecting to this organ are hypertrophied following the nerve growth because a correlation exists between the size of a neuronal cell body and the extent of arborization of neuronal processes served by that cell body. Growth factors, including NGF, are thought to be responsible for the signaling from target to neuronal soma and defining neuronal size. A disturbance in the amount of NGF produced would be expected to result in neuronal growth or recession. In the case of outlet obstruction, an increase in NGF production is associated with the smooth muscle hypertrophy following the obstruction of the bladder. NGF rises sharply and causes neuronal hypertrophy after inflammation.

Basic fibroblastic growth factor (bFGF) is one of the angiogenic, heparin-binding proteins and is associated with trophic, growth and survival effects on cholinergic ganglion cells and has been linked to the pathogenesis of BPH. In addition to animal and human data showing elevated bFGF mRNA with bladder outlet obstruction, bFGF has been shown to be increased in prostate cancer cell lines and in human prostate specimens containing adenocarcinoma. NGF, as well, is involved in the signaling between stromal and epithelial compartments of the prostate, suggesting a role in the prostate beyond signaling neural growth. bFGF has been assayed in normal human serum, urine and at elevated levels with malignancy and after surgery.

These clinical, electrophysiological and molecular observations show that bladder inflammation or growth could trigger structural and functional changes in afferents that contribute to irritative voiding symptomology. It is the disturbed voiding that affects patients lives most adversely and leads to active intervention. Treatments for BPH and IC have uncertain or temporary effectiveness, yet their cost is a significant portion of the health care budget and likely to increase. An inexpensive, substantiated urine test predictive of treatment outcome, useful for monitoring treatment or indicative of occult disease would profoundly advance the clinical management of BPH and IC.

The bladder is a smooth muscle organ requiring innervation for normal function and about which little was known concerning neurotrophism. The instant disclosure establishes NGF as a mediator of reflex changes following outlet obstruction. The regulation of NGF production by smooth muscle has profound implications to diseases involving innervated smooth muscle, including growth and inflammation as well as voiding dysfunction associated with denervation.

Prior data teaches that bladder afferents are altered in inflammatory and growth-associated voiding disorders, such as interstitial cystitis, inflammation and bladder afferents.

Significant increase in nerve fibers in the sub-urothelial and detrusor muscle layers in patients with IC, but not those with lupus-associated cystitis, indicates neurotrophic involvement. Cell types associated with IC inflammation, including mast cells, release substances that promote neural growth. Cystolysis, however reversed the sub-urothelial nerve proliferation. Many treatments for IC are based upon bladder de-afferentation, high-lighting the importance of this pathway in symptoms. Intravesical infusions of the sensory neurotoxin capsaicin have also been reported to reverse irritative voiding in IC, suggesting removal of the capsaicin-sensitive afferents ameliorates the symptoms. However, these treatments may ultimately be self-defeating. In the rat, denervation of the hemi-bladder increases bladder NGF and causes the remaining neurons to grow. An increased nerve fiber density is precisely what results from an increased supply of potent neurotrophic factors. Because neurotrophic factors regulate neural growth and afferent signaling in the adult, a role for factor-mediated neural changes is likely, before and after treatment. Therefore, it appears that bladder afferents grow and alter their responsive signaling after acute and chronic inflammatory stimuli in animals, and that IC in humans is also accompanied by nerve growth. Reinnervation can explain why the IC symptoms return or worsen after many treatments that could potentially cause denervation.

METHODS AND MATERIALS

The following methods were used in developing the data in the examples:

ELISA for NGF and NGF Antibodies

A two-site ELISA for NGF was adapted for use herein. 75 μl of 0.25 μg/ml anti-NGF (Boehringer-Mann) is adsorbed to NUNC certified immunoplates (96 well) in 50 mM Na carbonate buffer at pH 9.6 (2 hr.) and remaining sites blocked with 150 μl of 1.0% BSA in carbonate buffer for 1 hr. at 36° C. After washing in 0.4M NaCl in 0.1M $PO_4$ with 0.1% Triton X 100, the final wash is replaced with 50 μl of either sample or known amounts of NGF diluted in sample buffer in quadruplicate and incubated overnight at room temperature in a humidified chamber. The mouse NGF is freshly diluted in sample buffer for each assay. Each well then receives 50 μl of 10 mU/ml of beta-galactosidase linked anti-NGF in wash buffer for 2 hr. at 36° C., is washed, and then 50 μl of fresh MUG substrate solution added (1.0 mg methylumbelliferone β-galactopyranoside (Sigma, Pierce or BM) in 10 ml of 10 mM HEPES, 150 mM NaCl, 2 mM $MgCl_2$, 0.1% Na-Azide, 1% BSA, pH 7.0) for an incubation of 6 hrs. to overnight. The plates are read on a Fluoroscan II plate reader with a UV filter. Controls for the assay always include binding non-immune mouse IgG to the plate and the zero NGF point on the standard curve. Specificity for antibody binding to NGF was tested with insulin, a structurally similar molecule of a similar size. The standard curve for NGF typically is linear to 600 pg/ml, beyond which saturation occurred. However, 1 μg/ml insulin was below the level of detection. The monoclonal α-NGF used in this assay does not cross-react with a related neurotrophin, BDNF, but potential binding to NT-3 or NT-4 could not be assessed due to lack of sufficiently characterized reagents. Thus, some samples can contain levels of cross-reactive factors structurally similar to NGF. The assay is linear from 0.1 pg to 600 pg NGF and values for tissue contents are similar to published values (rat lung, spleen, heart atria, skeletal muscle). Significance of measured differences are determined by Student's t test.

Urine to be assayed for NGF is collected in 0.01% Na-azide, and stored frozen until assay. The urine is applied directly to the ELISA and tests as set forth heretofore.

Tissues or cells to be assayed for NGF are collected dry and frozen immediately on dry ice in weighed cryotubes and stirred at −70° C. Samples are shattered in an impact mortar under liquid nitrogen, then thawed in 4 volumes or a minimum of 1 ml PBS with 0.5% BSA, 0.1 mM PMSF, 0.1 mM benzethonium-Cl, 20 KIU/ml aprotinin, 2 mM benzamidine and 2 mM EDTA, homogenized, sonicated and centrifuged at 30,000 g for 60 min., all at 4° C. The supernatants are used for NGF quantitation. 150 ng authentic NGF is added to homogenate aliquots for recovery estimation, and an aliquot of the homogenate saved for protein and DNA assays. Conditioned medium samples are applied directly to the ELISA plate. Cell samples are solubilized in ELISA sample buffer, a lysing buffer with scraping to remove adherent material.

ELISA for bFGF and bFGF Antibodies

A protocol similar to the one for NGF has been developed for assay of bFGF but not yet applied to measurements in urine.

For in vivo experiments female Wistar rats weighing 200–300 grams were housed in individual cages, given routine rat chow and water ad lib.

Obstructed (OBS) Groups

In rats, a partial urethral ligation is used to create an infravesical obstruction. Following halothane anesthesia, the skin was shaved and prepped with iodine, and a midline incision made. The bladder was identified and the proximal urethra circumferentially dissected free from surrounding tissue. A 1.0 mm polyethylene tubing was placed alongside the proximal urethra and two 4.0 silk sutures were tied around both the urethra and the tubing. Subsequently, the tubing was removed creating a partial obstruction of the bladder. The abdominal incision was re-approximated using a two-layer closure of interrupted silk sutures.

Control rats undergo sham surgery in which a midline incision was made, the bladder identified, and the urethra dissected free from surrounding tissue. However sutures were not placed around the urethra. The abdominal incision was re-approximated using a 2-layer closure.

Histology

Under halothane anesthesia bladders are removed intact with a segment of urethra still attached. To standardize the conditions of muscle distention independent of the degree of enlargement, the bladders were fixed. After weighing the bladder, the urethra was cannulated with a 20 gauge needle and a ligature was placed around the needle at the bladder neck. The bladder lumen was filled with a fixative (1 ml of 10% formalin per 100 mg bladder weight) and the bladder was immersed in the fixative for 4 minutes. These bladders were then fixed overnight in 4% buffered formalin and stained with hematoxylin and eosin. Transverse sections cut at 14 μm were inspected with light microscopy for evidence of muscle hypertrophy.

Voiding Frequency

Voiding frequency was measured at various times after surgery in all groups. Absorbent filter paper was placed beneath the animal cages for a 3 hour period, 9:00 a.m.–12:00 p.m. Afterwards, urine markings were identified and counted. At least 4 separate measurements were obtained for each rat. No significant difference in water consumption was observed with a maximal inter-animal variability of 5 cc per day.

Cystometrogram

Obstructed (OBS) rats were anesthetized with urethane (1.2 g/kg, 0.75 sc, 0.25 ip) and had external jugular and carotid lines were placed for intravenous drug administration and blood pressure measurements, respectively. The abdomen was opened and a 21 gauge needle was inserted into the dome of the bladder. Polyethylene tubing filled with 0.9% saline connected the needle to Statham pressure transducer. Pressures were measured using a Gould RS 3600 rectilinear chart recorder. The bladder was filled at a constant rate of 0.1 cc/min. with 0.9% saline to obtain a pressure/volume curve. This was repeated in triplicate before and during IV infusion of 20 μg/kg/min. of verapamil dissolved in 0.9% saline. Compliance (change in volume to micturition divided by corresponding change in pressure), voiding pressures and micturition volumes were recorded.

Neuronal Labeling

Axonal tracing studies is performed on experimental and control rats to determine the degree of neuronal growth. The rats were anesthetized with halothane, a midline incision made, and the bladder isolated. Using a suspension of 4% wt./vol FloroGold (FG), from Fluorochrome, Inc., Englewood, Colo., 6–8 μl was injected into the bladder wall at 8 to 10 sites. A Hamilton syringe was used equipped with a 30 gauge needle. The needle was left in the bladder wall for 30 seconds then removed. After rinsing the bladder and the surrounding tissue with 0.9% saline, the abdominal incision was re-approximated with a double layer closure. Five days after injection of tracer, the rats were again anesthetized with halothane and the abdominal cavity opened. The MPG and the $L_6/S_1$ dorsal root ganglia (DRG) were identified and removed. The rats were sacrificed with intracardiac KCl. The MPGs and DRGs were fixed in 4% buffered formalin, washed in phosphate buffered saline (PBS), and equilibrated with successive PBS solutions containing 10, 20 and 30% sucrose. Cryostat sections (14 μm) were cut and placed on slides, mounted in PBS/glycerin, and cover slipped. FG-labeled ganglia were viewed using a Nikon FXA microscope equipped with UV fluorescence with the filter UV excitation at 360–380 nm.

Cross-sectional area profiles of all FG-labeled cells in every 3rd section were measured using a computerized image processing system and videomicroscopy. Video images were obtained through a 70 series camera at a magnification of 200X. The lower limit for cross-sectional areas was set at 150 μm$^2$ based on previous measurements of neurons in these ganglia.

Although the foregoing sets forth the methods employed in the examples, other methods of testing, as well as creating artificial obstruction, which produce the equivalent results, can be employed.

EXAMPLE I

NGF Rises Before Neuronal Growth

In humans, bladder outlet obstruction causes bladder growth and often, significant bladder hyperactivity. In the rat partial obstruction model, the bladder hypertrophies and the innervating neurons respond with neuronal growth and a change in the reflex pathway.

FIG. 1A graphs, over a seven week period, the increases in bladder weight, neuron size and voiding frequency that follow experimental partial outlet obstruction. Bladder weight increases sharply the first three weeks and stabilizes. Voiding frequency continues to rise fairly steadily throughout the period. Neuronal sizes in the major pelvic ganglion (MPG) rise after a one-week delay. The increase in neuron size also occurs after separation of the MPG from CNS connections. NGF is synthesized by the bladder smooth muscle, and levels also respond to mechanical stimuli. NGF tissue levels over the same time period are shown in FIG. 1B. NGF levels peak in the first week after an obstruction if normalized to cell protein or bladder weight, suggesting temporal correlation with the subsequent rise in neuronal size and voiding frequency. This example demonstrates that NGF drives neuronal remodeling after obstruction because changes in tissue NGF occur and precede the neuronal and reflex changes.

EXAMPLE 2

NGF Causes Neuronal Growth and Reflex Plasticity

The results above illustrate that neuronal form and function can be altered by an ongoing trophic interaction between the bladder and its innervation. The hypothesis that increased NGF production in hypertrophied bladder smooth muscle causes remodeling in the micturition pathways was tested. Normal and hypertrophied bladders were assayed for NGF, and the effect of endogenous antibody against NGF on the anomalous neuronal growth determined. Animals were immunized with purified NGF and levels of endogenous blocking antiserum confirmed by bioassay. A group of autoimmune animals were then subjected to experimental outlet obstruction, and neuronal areas of retrogradely labeled bladder neurons measured in the afferent $L_6$ and $S_1$ DRG's, as well as retrogradely labeled bladder neurons in the MFG. Immunity to NGF blocked the neural growth completely in the afferent DRG neurons (See Table 1). Not only was the growth in the size of bladder DRG cell bodies prevented by immunity to NGF, but an expansion in the central innervation field of these neurons was also prevented.

Bladders in the experimental animals were injected with wheat germ agglutinin-horseradish peroxidase (WGA-HRP) and the label allowed to transport to the central field of bladder sensory afferents in the sacral parasympathetic nucleus. The obstruction-induced expansion of the WGA-HRP label in the sacral parasympathetic nucleus was prevented by immunity to NGF (Table 1). Obstruction also induced re-expression of the growth-associated protein GAP-43 by DRG terminals in the SPN innervation field, and immunity to NGF suppressed GAP-43 expression, as well (Table 2). GAP-43 is a G-protein related factor expressed in growing axons.

TABLE 1

Effect of Immunity to NGF on Obstruction-Induced Afferent Plasticity

|  | NGF Immune | OBS + Immune | OBS |
|---|---|---|---|
| $L_6/S_1$ DRG Area (mean μm$^2$ ± SE) | 529 ± 116 | 576 ± 165 | 766 ± 377 |
| HRP Area in SPN (mean μm$^2$ × 10$^3$ ± SE) | 2.1 ± 0.16 | 2.0 ± 0.30 | 3.9 ± 0.21 |

(n = 4 rats, 150 DRG neurons and 25 spaced sections analyzed/rat) (HRP = horseradish peroxidase tracer; SPN = Sacral parasympathetic nucleus)

TABLE 2

Effect of Immunity to NGF on GAP-43 Expression in SPN GAP-43 Optical Density (% above background)

| Normal | Obstructed | NGF Imm ± OBS |
|---|---|---|
| 6.6 ± 4.3% | 26.7 ± 6.5%* | 3.0 ± 2.8%* |

NOTE:
Data are expressed as percent area labeled of a standard 200 μ$^2$m grid centered on the SPN in cryostat sections labeled immunohistochemically for GAP-43, using a monoclonal antibody (Boehringer-Mannheim). The area labeled was defined by thresholding digitized images. (n = 3 rats). * = p < 0.05 compared to control; p < 0.005 compared to obstructed).

The foregoing further illustrates that the growth and remodeling in the afferent micturition pathways is mediated by obstruction-induced increases in the neurotrophic factor, NGF. Immunity to NGF also prevented the increase in voiding frequency (p<0.05) and increased spinal reflex associated with the obstruction. This indicates that the functional changes in voiding that accompany obstruction also derive from the NGF-driven alterations in the bladder afferents. Results in the MPG were similar, but the blockade of MPG growth by immunity to NGF was less complete.

EXAMPLE 3

Reversal of Neuronal Growth is Incomplete

Further testing demonstrated aspects of the control of NGF production in bladder. Reversal of the changes that accompany obstruction was tested. Animals that had been experimentally obstructed for six weeks had a second surgery to relieve the obstruction, and then were examined after another six weeks. In these cases, the elevated voiding frequency was reversed, and the bladder decreased in weight toward normal. However, the changes in neuronal area failed to completely reverse, and NGF remained higher than the control. This result helps to explain the failure of surgery to consistently relieve the sensory symptoms associated with obstruction in patients. Up to 60% of cases with BPH-induced hyperactive bladder signs fail to experience relief despite a return to normal flow rates, indicating that the plasticity induced through chronic excess neurotrophin is not always readily reversible. However, if NGF and bFGF remain elevated after treatment, the process of neural remodeling can actually be reversed when factor levels are returned to normal.

EXAMPLE 4

Involvement of Additional Factors

Not all of the growth in the MPG was blocked by immunity to NGF and many of the neurons in the MPG are not killed in vitro by blocking antibodies to NGF, indicating that many bladder neurons respond to other, non-neurotrophic factors. Also, it is possible that the apparently NGF-responsive neurons are actually responding not to NGF but to a close family member, BDNF, NT-3 or NT-4/5. This was examined by determining the response of MPG neurons in in vitro survival assays to other factors and to antibodies specific to authentic NGF.

MPG's were dissected from adult (220–300 g), female Wistar rats under halothane/oxygen anesthesia, cleaned and dissociated for culture. Ganglia were soaked in collagenase/trypsin in saline on ice for 45 min., then incubated at 37° C. for 45 min. to facilitate mechanical dissociation. Cell suspensions of MPG were plated into collagen-coated 24-well microwells in Dulbecco's modified Eagle medium (HG) (GIBCO) with 10% (v/v) horse serum and 10% fetal bovine serum at approximately 1000 neurons per well (500/cm$^2$). One-half of the 1 ml medium volume per well was refreshed every other day. Test substances were added at the concentrations indicated: NGF was purified murine 2.5S NGF obtained from E. M. Johnson, Jr. (Washington University, St. Louis). bFGF: recombinant human (UBI, Inc., Lake Placid, N.Y.) Anti-bFGF: monoclonal IgG1 (UBI, type I, blocking). CNTF: Recombinant rat (PeproTech, Inc., Rocky Hill, N.J.). Conditioned medium was standard medium conditioned for 24 hrs by cultures of rat detrusor smooth muscle and used without dilution. Bladder extracts were created by homogenizing normal whole bladder in saline and were added to the test medium at 1:10 (v/v). Neuronal survival after 5 days in culture was determined by direct cell counting under phase contrast optics at 200X magnification of round, smooth, bright neuronal somata. 5.4% of the total area across a diameter of each microwell was observed and the number of surviving neurons counted used to estimate the total in the culture, a procedure known to yield reliable estimates of neuronal survival. The total number of neurons counted per culture varied with the degree of survival, from 10 to >75. Based upon the average plating density, neuronal survival in control cultures was 61%±12.7% (SE) of the neurons plated. Differences in mean neurons surviving were tested for significance using the paired Student's t test of SPSS/PC+ or, for multiple comparisons, ANOVA in Statisica. 7–20 separate wells were used for each test condition and the experiments covered five separate platings.

The anti-serum specific to NGF was produced against purified murine 2.5S NGF in goat and provided by the laboratory of Eugene M. Johnson, Jr. It has been tested by specific bioassay and found to lack cross-reactivity to the structurally similar BDNF and NT-3 neurotrophins. The unfractionated goat antiserum was affinity purified using 2.5S murine NGF cyanogen-Br linked to sepaharose 4B. 100 ng/ml of the resultant product completely blocked the activity of 5 ng/ml 2.5S NGF in a chick DRG fiber outgrowth bioassay.

Figure 3:
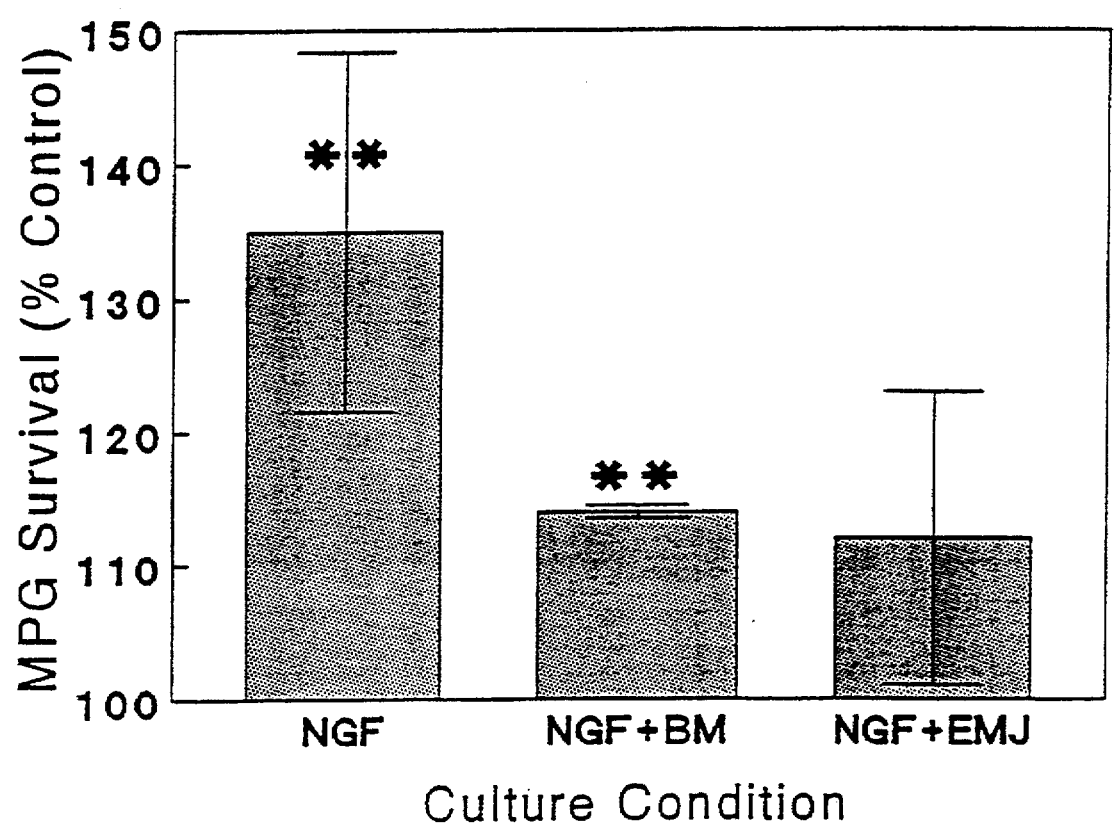
FIG. 3 illustrates the effect of NGF and anti-NGF on survival of MPG neurons in cell culture.

Exogenous NGF (50 ng/ml) added to the medium increased survival of neurons from the MPG in dissociated cell culture 35%±13.3% above the control level (FIG. 3). The increase in survival was blocked by monoclonal anti-NGF (Boehinger-Mannheim) and by the specific, purified, non-cross-reactive poly-clonal anti-NGF. This indicates that adult MPG neurons respond to NGF as neuronal survival in cultures without added NGF, but with either antibody, was not significantly different from control (n=8 ea., data not shown).

Figure 4:
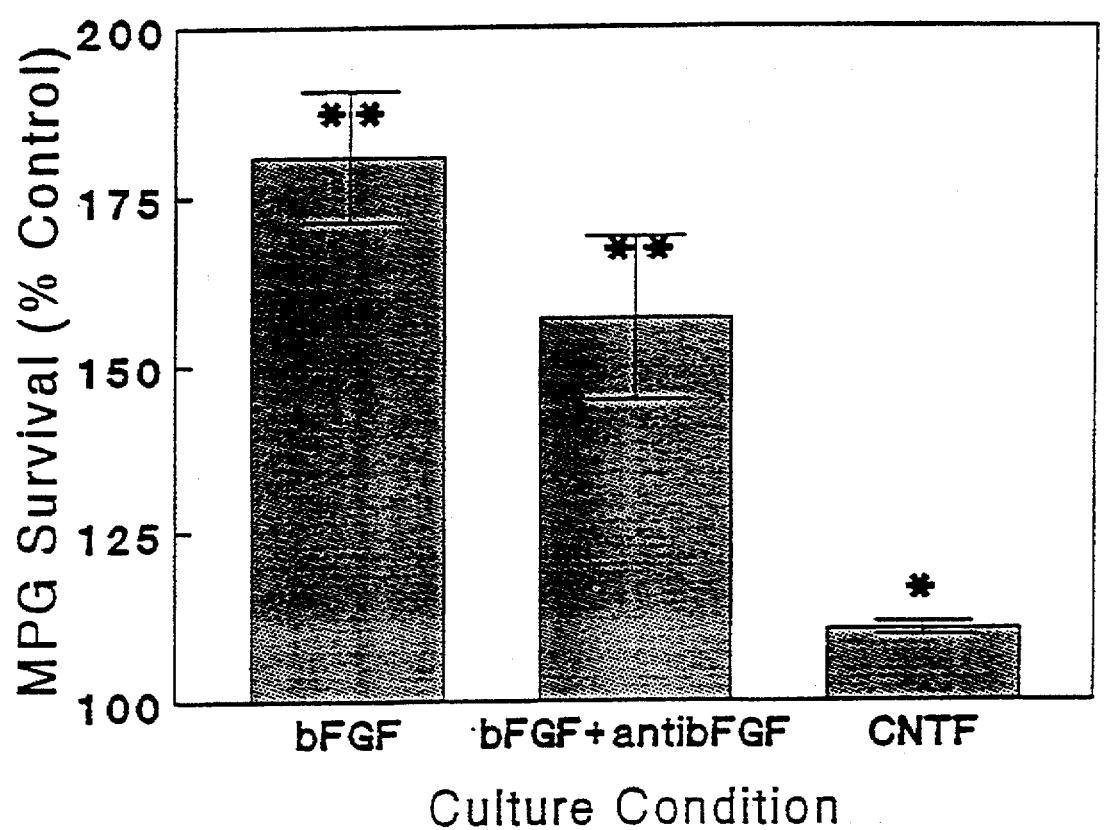
FIG. 4 illustrates the survival of MPG neurons in cell culture: Effect of bFGF, A-bFGF and CNTF.

In vivo, a subset of MPG neurons may obtain NGF from the bladder. Smooth muscle from the bladder secretes significant levels of NGF in culture. Therefore, the ability of anti-NGF monoclonal antibody to block survival support by conditioned media from cultured bladder muscle as well as extracts of whole bladder was tested. The survival of MPG neurons grown in conditioned medium from bladder muscle cell cultures was reduced to 72%±4.1% of control by 100 ng/ml anti-NGF antibody (p<0.05, n=7). Conditioned medium alone had a variable effect on neuronal survival, with increases up to 26% or decreases to 72% of control in different experiments. Neuronal survival in cultures with medium supplemented by bladder tissue extracts was reduced (81%±1% of control, p=0.086, n=3) in the presence of antibodies against both NGF (100 ng/ml) and bFGF (200 ng/ml). Anti-NGF alone in the medium with bladder extract had no significant effect upon neuronal survival. The bladder extracts added to the medium alone also had a variable effect from no difference to an increase of 30% over control in different experiments.

bFGF (100 ng/ml) increased MPG neuronal survival to 81%±9.6% above the control value, as shown in the graph of FIG. 4. 200 ng/ml blocking antibody against bFGF added to the medium significantly inhibited, but did not completely reverse, the effect on survival. CNTF slightly elevated neuronal survival (10%±0.5% above control, p=0.054).

As disclosed herein, MPG neurons respond to authentic NGF, further supporting a role for NGF in neural plasticity in this visceral reflex pathway. Testing indicates that if the neurons were responding to related, non-NGF factor(s) in these experiments, the specific anti-NGF antiserum would not be effective in preventing neuronal survival in vitro. MPG neurons also respond to bFGF and CNTF in vitro. mRNA levels for bFGF have been reported to increase following bladder outlet obstruction. Thus bFGF, in combination with NGF can induce neuronal plasticity following hypertrophy. Additionally, bFGF has been reported to increase NGF secretion in some types of cultured cells including vascular smooth muscle but to decrease NGF mRNA slightly in other cell types.

Because antibodies against both bFGF and NGF were required to block the enhanced survival with bladder extracts, muscle cells in vivo can produce both factors. NGF is synthesized and secreted by smooth muscle in culture and present in supernatants of homogenized bladder. The NGF gene includes a consensus signal sequence for extracellular transport. bFGF, on the other hand, lacks a recognizable signal sequence and often has been found to be retained by cells unless cellular integrity is disrupted, such as with homogenization. However, bFGF secretion by some cell types has been reported. Thus, examination was made of bladder extracts as well as conditioned medium to ascertain whether bFGF antibody was equally effective in both cases. The data further confirm that NGF is the active component of conditioned medium but both NGF and bFGF are active in extracts.

CNTF was discovered via an in vitro survival assay using cholinergic parasympathetic neurons. The rat MPG is composed predominantly of cholinergic parasympathetic neurons which provide input to the bladder and penis, thereby responding to CNTF. The survival of parasympathetic neurons is also increased in response to bFGF.

EXAMPLE 5

Bladder Inflammation Also Causes Elevated NGF and Neuronal Growth

Bladder outlet obstruction is one of several causes of changes in voiding patterns and symptomology. Inflammatory conditions such as interstitial cystitis also result in irritative voiding patterns and pain, suggesting that these conditions may also involve changes in the neural pathways to the bladder. The was tested in animal models of bladder inflammation.

Normal voiding frequency in rats (0.66/hr., n=8) is increased to a mean of 1.8/hr. (n=4) at 3 days after intravesical instillation of 0.2% formalin, demonstrating an irritative voiding condition. This dose of formalin is well-tolerated but effective at causing the inflammation-induced voiding increase. In order to confirm a relationship between acute inflammation and afferent activity, animals under urethane anesthesia were prepared for peripheral fiber multi-unit recording during instillation of 0.2% formalin into the bladder via urethral catheter.

Figure 2:
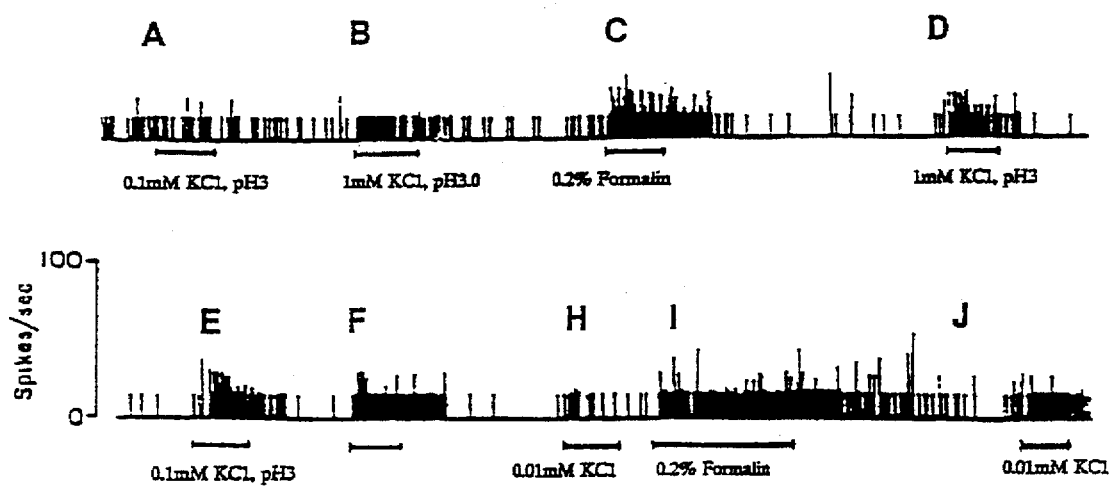
FIG. 2 is a graph of ratemeter records of frequency of afferent firing in rats with intravesical agents.

FIG. 2 illustrates the ratemeter records of frequency of afferent firing with intravesical agents. The record demonstrates that afferent firing in bladder nerves of the urethane anesthetized rat is minimal from the non-distended bladder (A and between letters). Distension with saline or a low concentration of KCl (0.1 mM) to a volume equal to one-half (0.3 ml) of that which triggers micturition has little influence on firing rate in the normal bladder (A,H). However, instillation of higher concentrations of KCl (B) with pH=3.0 does induce an increase in firing. Following intravesical formalin (C,D) an increase in firing rate occurs accompanied by a rise in mean blood pressure (not shown), an indication of activation of nociceptive pathways. Subsequently, the threshold for KCl induced increases in firing is lowered (E,F,J).

These tests as well as those of others with single afferent recording have shown that the threshold for mechanoreceptive afferents is reduced after formalin instillation. Furthermore, the mechanoreceptive afferents firing in response to formalin are subsequently responsive to KCl solution, not just mechanical stimulation. Finally, unmyelinated, presumed nociceptive, bladder afferents become mechanosensitive after an acute inflammatory stimulus. These tests indicate acute irritative stimuli can alter afferent firing characteristics within a short time frame. Tests have also shown a link between inflammation and NGF production in the bladder and that tissue NGF levels are elevated by bladder inflammation. These tests used xylene or formalin instillation and mechanical irritation to cause inflammation. Xylene is another effective chemical inflammatory agent. 24 hours after xylene instillation, bladder weight was increased 70% above control and NGF per bladder was increased 190%. Mechanical inflammation had a similar effect: bladder weight was increased 97% over control and NGF content doubled (n=4). Expressed as pg NGF/gm wet weight, xylene caused a 70% increase in NGF (control=17 pg/gm wet weight), while mechanical inflammation resulted in a 51% increase. This increase in tissue NGF was associated with neuronal growth. When 500 neuronal area profiles were measured in two rat major pelvic ganglia 2 weeks after formalin instillation, the mean profile ($444\mu^2$) was significantly elevated over control ($340\mu^2$). Area profiles of the bladder sensory neurons were also increased by inflammation.

EXAMPLE 6

Blocking Agents Used to Minimize NGF Production

Micturition requires the coupling of central neural input to the $Ca^{++}$-dependent contraction of bladder smooth muscle. These processes are altered following obstruction of the urinary bladder. In the rat, obstruction induced by partial urethral ligation decreases bladder emptying and increases voiding frequency. Decreased emptying of the obstructed bladder has been explained on the basis of impaired smooth muscle contractility. On the other hand, increased urinary frequency has been attributed to either changes in reflex pathways governing voiding, alterations in electromechanical coupling in smooth muscle, or elevations in residual urine volume. In response to the mechanical stress of urethral obstruction, smooth muscle hypertrophy occurs coincident with alterations in the size and connectivity of sensory and motor nerves supplying the bladder. This neuroplasticity relies on the synthesis and release of NGF by smooth muscle cells and the uptake of this neurotrophic factor by bladder nerves.

When some of the voiding disturbances include increased NGF production causing neuroplasticity, then reducing NGF production by the bladder can have a therapeutic effect. The drugs currently used to treat voiding dysfunction include anti-cholinergics, adrenergic inhibitors, tri-cylic anti-depressants and anti-inflammatory agents. None have been shown to affect NGF dynamics in the bladder.

A similar situation exists in the cardiovascular system. Vascular smooth muscle produces nerve growth factor. In spontaneously hypertensive rats, the vasculature receives an increased symptomatic innervation due in part to an increased NGF production by hyperplastic and/or hypertrophic muscle. Hypertension in humans is treated with a variety of treatments and medications. These include altered diet and exercise, diuretics, beta-blockers, $Ca^{++}$ channel blockers, ACE (angiotensin converting enzyme) inhibitors, vasodilators, such as verapamil, diltiazem and prazosin, and adrenergic inhibitors. The treatments are intended to lower blood pressure, each working through a specific mechanism of action. For example, diuretics reduce blood pressure by reducing water retention thus reducing filling of the cardiovascular compartment. Beta-blockers and $Ca^{++}$ channel blockers relax vascular smooth muscle, reducing blood pressure by reducing vascular resistance. In each case, the goal is to lower mean arterial pressure, thus reducing the stress on vessels and perhaps preventing further abnormal growth.

These two cases, bladder and vascular smooth muscle, indicate a link between smooth muscle growth, perhaps driven by mechanical forces, and subsequent pathophysiological changes in the neural control of the smooth muscle organs. An apparent link is NGF. Therefore, reducing the output of NGF by smooth muscle, by administration of a blocking agent, will have a beneficial therapeutic effect. None of the drugs currently used to treat disturbances in voiding or hypertension have been shown in the prior art to reduce NGF production by smooth muscle, although some might be expected to have an effect. Diuretics affect fluid and ion transport in the kidney and would not be expected to have an effect. Beta-blockers increase NGF production, having the opposite affect on smooth muscle. $Ca^{++}$ channel blockers are used for hypertension, cardiac arrhythmias and angina but are not associated with changes in innervation or NGF. ACE inhibitors lower blood pressure by preventing the production of angiotensin, a vasoconstrictive agent. Angiotensin II by itself has no effect on NGF production although when paired with adenosine it increases NGF output. It is unknown at this time whether the ACE inhibitors will reduce NGF output. Vasodilators relax vascular smooth muscle by affecting muscle contraction. The adrenergic inhibitors are used clinically both to treat hypertension and to prevent hyperactive voiding. The α-adrenergic receptors increase NGF output by vascular smooth muscle, thus blocking them might be expected to reduce NGF output but data on actual effects is lacking.

It is known that $Ca^{++}$ is a central regulatory signal for all cells, including smooth muscle. Intracellular $Ca^{++}$ regulates contraction, cellular growth and the energy metabolism of the muscle cell. While $Ca^{++}$ channel antagonists inhibit $Ca^{++}$ entry into the cell from the extracellular fluid, the effect is specific for certain types of $Ca^{++}$ channels. Many $Ca^{++}$-channel blockers, such as verapamil and diltiazem, are known to block entry via the L-type, voltage activated $Ca^{++}$ channels but to have little or no effect on other channels. Therefore, $Ca^{++}$ channel antagonists would not be expected to affect NGF metabolism since NGF does not interact with L-type channels. However, the effect of $Ca^{++}$ channel antagonists on bladder weight gain, NGF production, and changes in neuronal size following obstruction of the urethra in the adult rat was investigated. Drugs were administered in the drinking water to rats ad lib, and their effect on post-obstructive voiding and neuronal growth determined.

Bladder Histology and Weight

Figure 6:
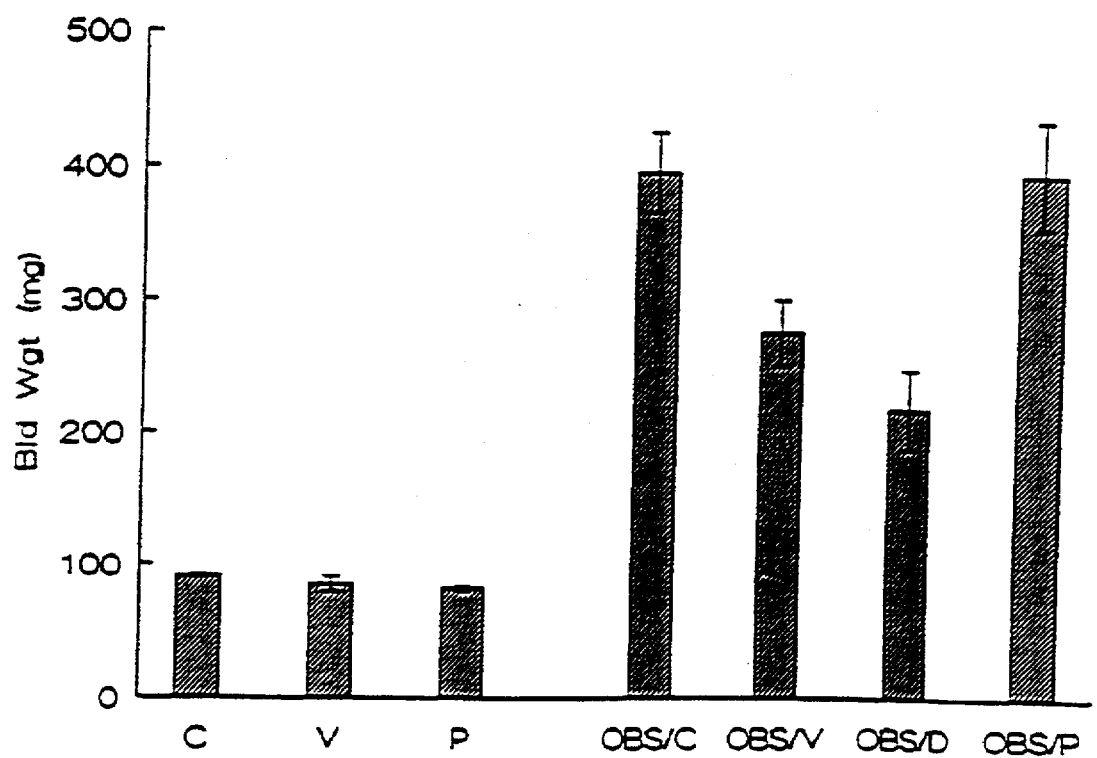
FIG. 6 is a graph illustrating bladder weights in control animals receiving water alone, verapamil or prazosin for 3 weeks, compared to obstructed rats receiving water, verapamil, diltiazem and prazosin.

As shown in FIG. 6, bladder weight in the control (C) group (86±2 mg) was not affected by verapamil (V 80±2 mg), or prazosin (P 83±2 mg). Partial urethral ligation produced a 4.3 fold increase in mean bladder weight over controls (OBS 397±30 mg). Prazosin-treated obstructed rats (OBS/P) experienced similar increases in bladder weight (396±40 mg). Obstructed animals given $Ca^{++}$ channel blockers, however, experienced only a 2 to 3 fold increase in bladder weight (OBS/V 277±25 mg, OBS/D 219±30 mg). No difference was found in mean body weights or water consumption for any group. Thus, following obstruction, $Ca^{++}$ channel blockers allowed only 55–70% of the usual gain in bladder weight to occur. Histological examination of bladder tissue suggested that the reduction in the increased bladder gain was due, in part, to changes in muscle mass. This is due to less protein content per wet weight bladder in OBS/V (77 µg prot/mg), and OBS/D (42 µg prot/mg) compared to that observed in OBS (124 µg prot/mg) animals.

Voiding Frequency

Figure 5:
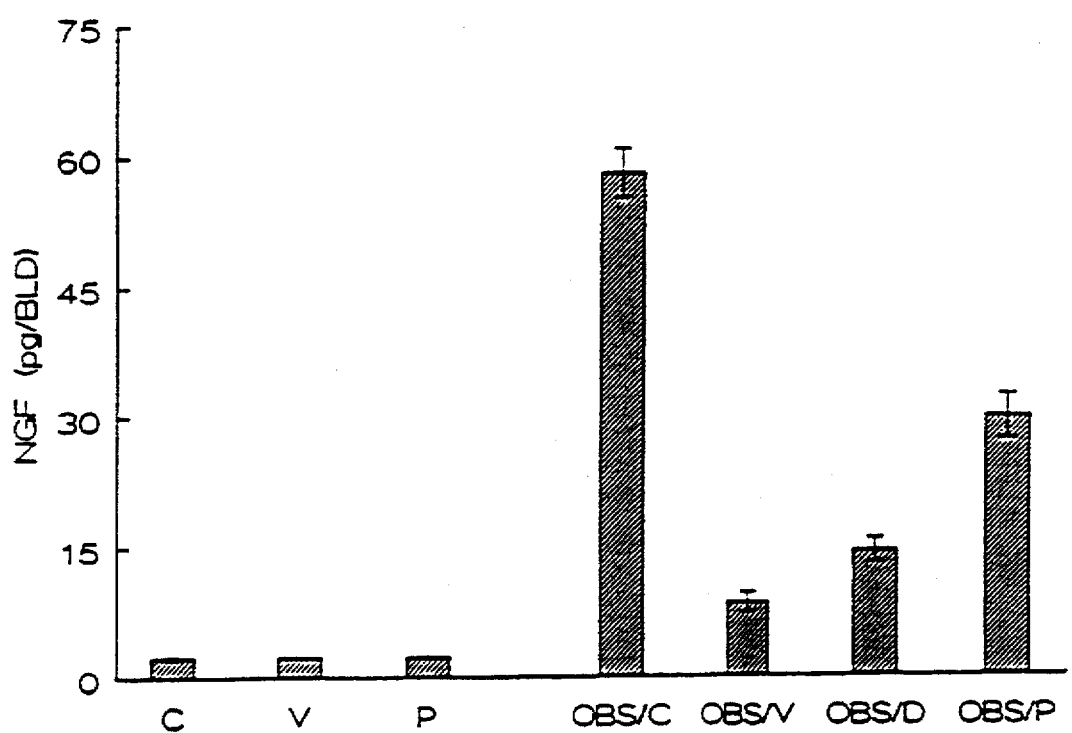
FIG. 5 is a graph showing the drug effects on bladder NGF following outlet obstruction in rats compared to obstructed rats receiving water, verapamil, diltiazem and prazosin.
Figure 7:
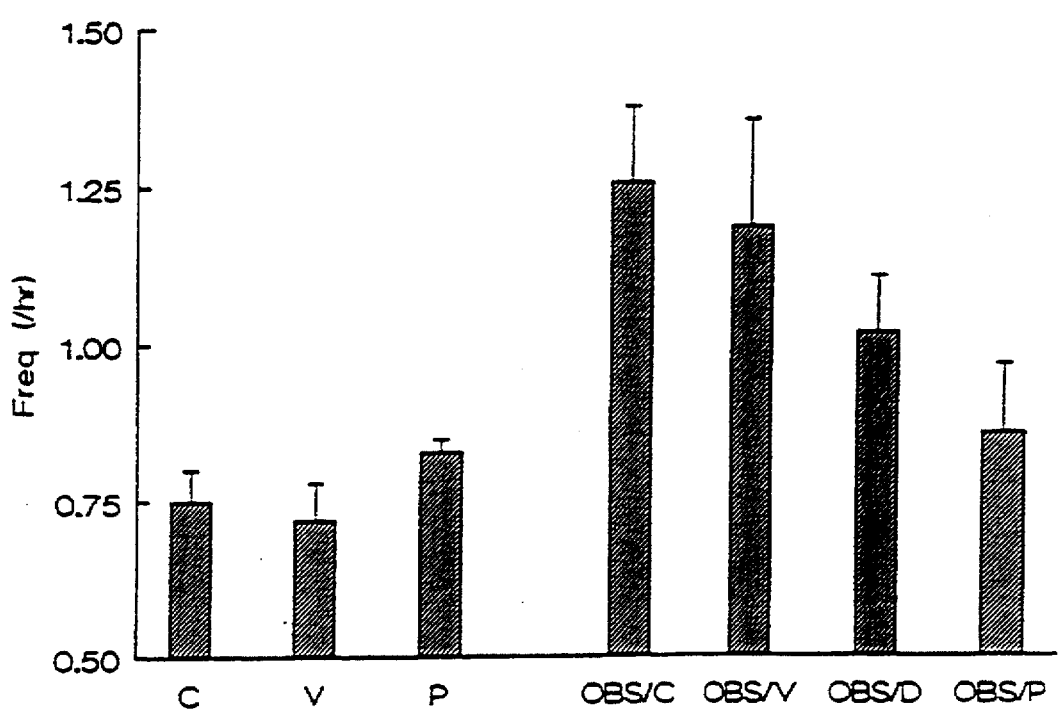
FIG. 7 illustrates the voiding frequencies in control groups receiving water, verapamil or prazosin for 3 weeks.

Voiding frequencies for the 3 control groups were similar regardless of drug treatment (C 0.75±0.05 hr.$^{-1}$, V 0.72±0.06 hr.$^{-1}$, P 0.92±0.03 hr.$^{-1}$) and is illustrated in the graph of FIG. 7. As previously reported, obstruction causes a significant increase in voiding frequency to 1.26±0.12 hr.$^{-1}$. A similar increase was observed in obstructed animals treated with $Ca^{++}$ channel blockers (OBS/V 1.19±0.17 hr.$^{-1}$, OBS/D 1.02±0.09 hr.$^{-1}$). The increase in the voiding frequency in obstructed animals was not observed, however, in the rats that received prazosin, (1.26 hr.$^{-1}$ in OBS) (0.86±0.11 hr.$^{-1}$). The rats receiving prazosin had a voiding frequency that was not significantly different from the rats in group C. Thus, prazosin prevented the increase in voiding frequency observed with obstruction. These results are illustrated in the graph of FIG. 5.

Micturition Reflexes

Acute administration of verapamil (20 µg/kg/min. IV), while reducing mean systemic blood pressure by 11.7±2.3 mm Hg, had no dramatic effect on micturition threshold volume (1.7±0.7 cc, vs. 1.6±0.7 cc), voiding pressure (32.8±6.2 mm Hg vs. 28.7±7.4 mm Hg), or compliance (0.79±0.63 cc/mm Hg vs. 0.52±0.26 cc/mm Hg) in the obstructed animals.

Neuronal Size

Figure 8:
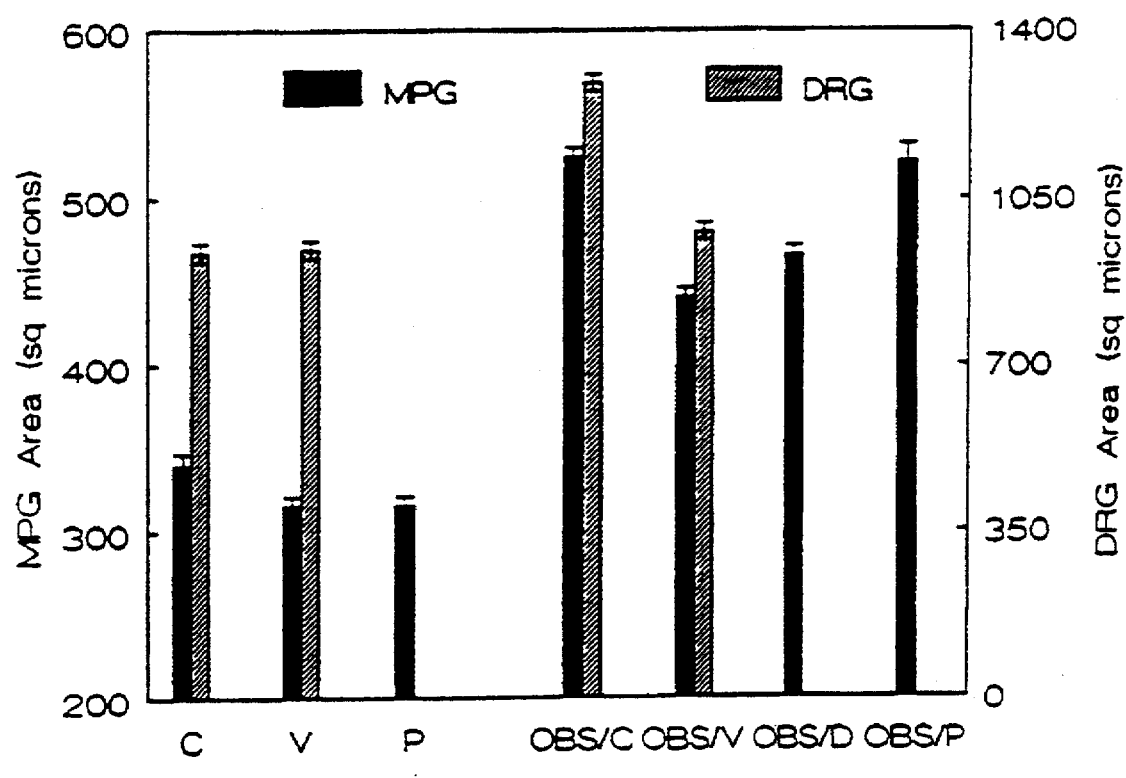
FIG. 8 show in a graph the mean neuronal area profiles for retrogradely labeled neurons in the major pelvic and $L_6$ and $S_1$ dorsal root ganglia in controls compared to obstructed animals.

As shown in the graph of FIG. 8, obstruction produced hypertrophy of neurons in both the $L_6$ and $S_1$ DRG and MPG. MPG neurons from obstructed animals had a mean cross-sectional area profile of 525±5.6 µm$^2$ (684 cells), compared to 340±5.0 µm$^2$ for C neurons (761 cells). Area profiles for DRG neurons also increased, [OBS 1290±18 µm$^2$, (417 cells) compared to CONT (939±20 µm$^2$, 361 cells)]. $Ca^{++}$ channel blockers and prazosin had no effect on area profiles for MPG principal cells in unobstructed rats (C,V,P groups). However, in the six obstructed rats, $Ca^{++}$ channel blockers prevented 15% of the growth in MPG cell size (OBS/V 442±10.6 µm$^2$, 778 cells, OBS/D 466±8.7 µm$^2$, 750 cells), compared to OBS/C animals (525±5.6 µm$^2$, 701 cells) (p<0.05). DRG neurons demonstrated an even more dramatic inhibition of the expected increased cross sectional area (OBS/V 981±18 µm$^2$, 365 cells) compared to OBS (1291±18 µm$^2$, 380 cells) (p<0.001). Prazosin did not affect the neuronal hypertrophy associated with obstruction in the MPG (522±10.4 µm$^2$, 350 cells). DRG cells were not measured in prazosin or diltiazem groups.

NGF Levels

Figure 9:
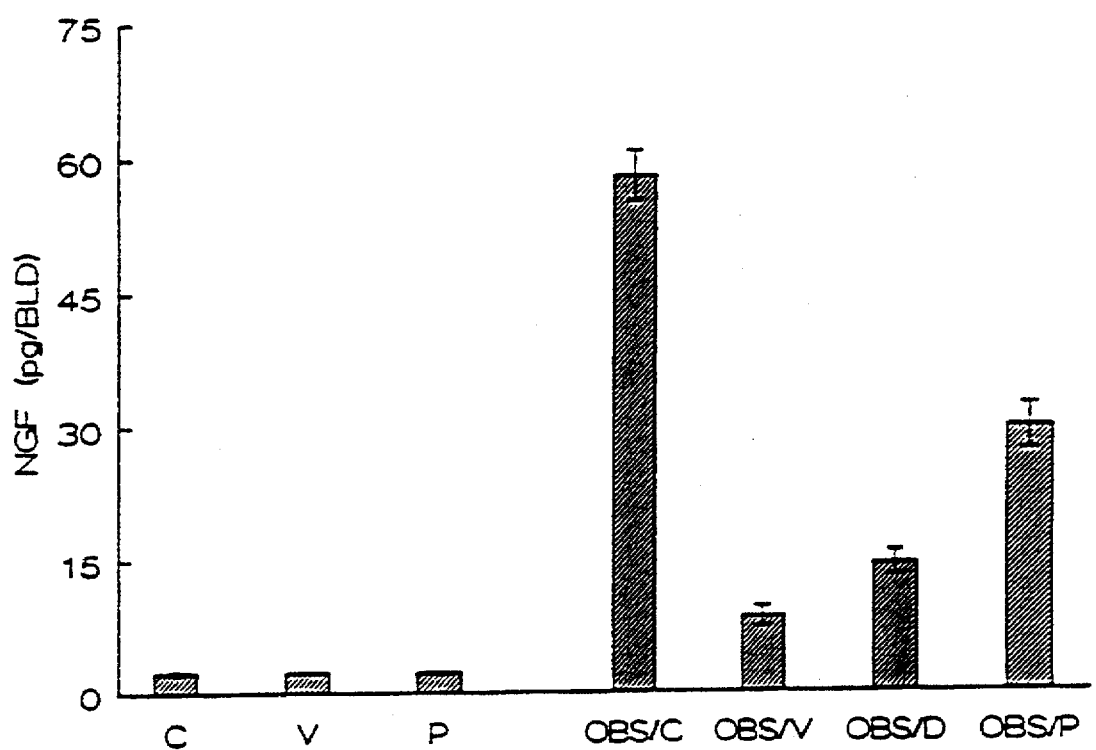
FIG. 9 graphs the total NGF content in the bladders of controls 3 weeks after obstruction.

Tissue content of NGF was markedly elevated in OBS (58.2±0.02 pg NGF/bld) compared to C animals (2.29±0.15 pg/bld), as shown in FIG. 9. Verapamil and prazosin did not affect NGF levels in the control groups (V 2.29±0.2 pg/bld, P 2.29±0.09 pg/bl). However, prazosin nearly halved obstruction-induced increases in NGF (OBS/P 30.0±0.4 pg/bld). Verapamil and diltiazem given to obstructed animals produced an even more pronounced inhibition of the rise in NGF (OBS/V 8.5±0.2 pg/bld, OBS/D 14.5±1.4 pg/bld). The lower NGF levels were also noted per protein (OBS 0.47 pg/mg prot, OBS/V 0.11 pg/mg prot, OBS/D 0.22 pg/mg prot) and per DNA content (OBS 1.58 pg/µg DNA, OBS/V 0.36 pg/µg DNA, OBS/D 0.69 µg/DNA) demonstrating the effect on NGF content was over and above the influence on total protein or total DNA.

Measurements and Cytosolic $Ca^{++}$

A significant difference (p<0.05) was noted in basal $Ca^{++}$ levels from muscle cells derived from obstructed animals (258±11 nM, n=6) compared to those from untreated control adults (314±14 nM, n=5). These findings suggest a disturbance in $Ca^{++}$ homeostasis that remains 1 week after subculture in vitro. Smooth muscle cells derived from neonatal rats and grown for 1 week in culture medium containing verapamil (10 µM) had markedly elevated cytosolic $Ca^{++}$ 590±24 nM (n=5) compared to a basal level of 282±6.5 nM, (n=17) in cells not cultured in the presence of this $Ca^{++}$ channel blocker.

Figure 13:
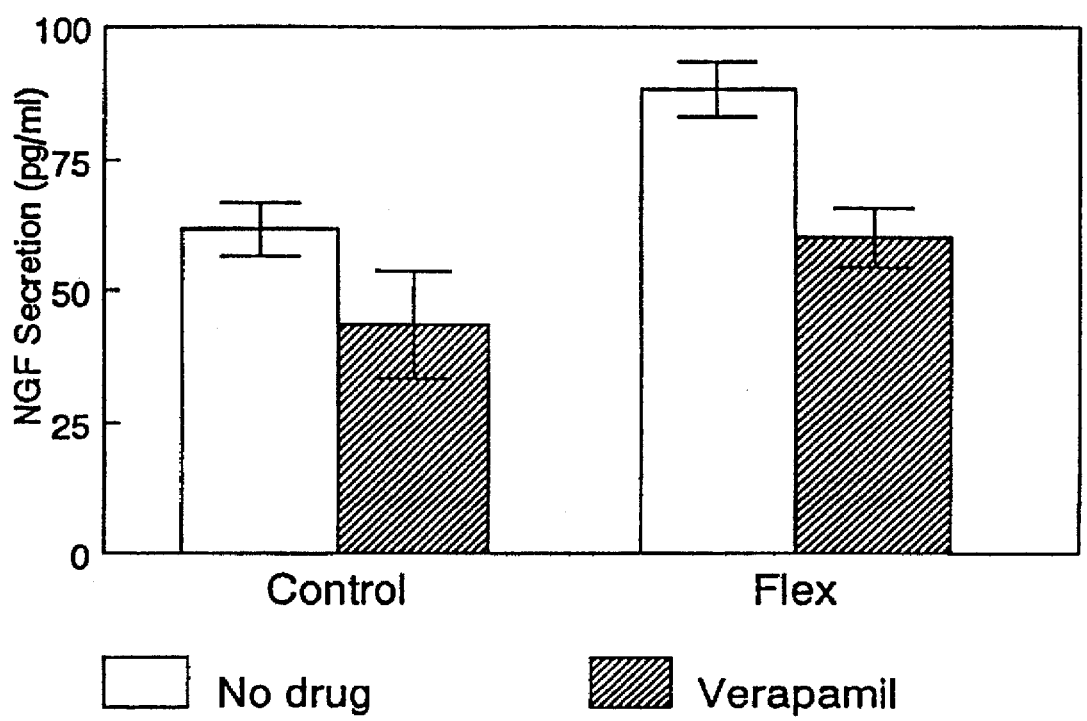
FIG. 13 is a graph illustrating the effect of verapamil on NGF secretion stretched and control cultured bladders.

The effectiveness of the $Ca^{++}$ channel antagonist verapamil was also tested at reducing NGF secretion by bladder muscle in culture. Verapamil was chosen as a representative example of L-type $Ca^{++}$-channel antagonist due to availability and, therefore, lower patient cost. As illustrated in the foregoing Examples, other $Ca^{++}$-channel antagonists have produced favorable results, and it is expected that they will produce similar results when tested using the protocol of this Example. In this instance, rat bladder smooth muscle from normal, adult Wistar rats was adapted to cell culture, using methods in commonly known in the prior art, and verified as smooth muscle by specific immunohistochemistry. The muscle was cultured in tissue culture dishes with a collagen-coated, flexible lower surface, thus allowing a vacuum to be applied to the bottom of the dish. The vacuum pulls the dish bottom downward, thus mechanically stretching the muscle. NGF secretion by the cultured muscle was monitored by sampling the culture medium at specific times before, during and after stretching the cultures at 20% elongation for 10 second cycles at 3/minute. Stretched cultures were compared to control, unstretched ones and verapamil (10 µM) was added to the culture medium to test its effect. Representative results appear in FIG. 13.

The stretching protocol elevated NGF secretion above basal rates. After 6 hr., verapamil decreased basal NGF secretion 15–34% (p<0.05) in 4 experiments using the above protocol, reducing the stretch-induced secretion by a comparable 19–34% (p<0.05). These data indicate that the $Ca^{++}$ channel antagonist reduced basal NGF production and stretch-activated NGF production in this model system in vitro. However, the drug did not prevent the normal increase in NGF due to mechanical stretching. Thus, the $Ca^{++}$ channel antagonist did not eliminate an apparently normal compensatory reaction to mechanical stress but did effectively depress basal and stretch-induced NGF secretion. This unexpected result indicates that the $Ca^{++}$ channel antagonist has effects on cellular regulation of NGF output that are independent of inhibition of L-type $Ca^{++}$ channels. Voltage-activated $Ca^{++}$ channels are not known to control NGF secretion and are not active under normal, resting conditions. These channels have also not been implicated in the cellular response to mechanical force, and were ineffective in preventing increased NGF secretion caused by stretch.

As disclosed herein, $Ca^{++}$ channel blockers partially prevent the growth of muscle and nerve in response to increased mechanical stress. The effect of verapamil and diltiazem is most likely due to an alteration in cytosolic $Ca^{++}$ because these antagonists of voltage-regulated $Ca^{++}$ channels produced similar responses. Furthermore, prazosin which reduces smooth muscle tone in the bladder neck and urethra did not influence muscle or nerve growth.

The increase in bladder weight following partial urethral ligation in the rat is primarily due to an increase in smooth muscle. However, there is also an increase in the extracellular matrix. The reduced increase in protein and DNA content following administration of $Ca^{++}$ channel blockers in obstructed animals confirms that verapamil and diltiazem diminish cellular mass rather than non-cellular material. Histologic examination of bladder tissue following obstruction in verapamil and diltiazem-treated animals also suggests these drugs affect smooth muscle growth. Verapamil and diltiazem in unobstructed rats did not effect bladder weight or neuronal area profiles.

Retrograde axonal labeling experiments showed that $Ca^{++}$ channel blockers attenuated the increases in cross-sectional area profiles of afferent and efferent neurons supplying the bladder in response to chronic obstruction. This decreased neuronal growth correlates with a reduction in NGF in obstructed bladders maintained on $Ca^{++}$ channel blockers. The relatively smaller decrease in NGF in prazosin-treated rats compared to those receiving the $Ca^{++}$ blockers can explain why significant changes in neuronal size were not detected in animals receiving this alpha adrenergic blocker.

Verapamil and diltiazem can also affect basal cytosolic $Ca^{++}$ levels and blunt growth through a direct action on neural tissue. Neurons with lower levels of cytosolic $Ca^{++}$ are less responsive to NGF. Total tissue NGF, as well as the amount per unit of protein or DNA, was reduced which indicates a decrease in cellular production through translation, transcription or degradation.

Diltiazem, verapamil and prazosin did not influence voiding frequency in the absence of obstruction, indicating that changes did not occur in urine production, smooth muscle contractility and neurotransmission via central and peripheral autonomic pathways.

Treatment of urethral-ligated rats with prazosin prevented the increase in voiding frequency but did not inhibit cellular growth. Prazosin, an alpha-1 adrenergic antagonist, inhibits contractions of bladder and urethral smooth muscle in vitro and has been shown to prevent myocardial hypertrophy in response to increased mechanical stress. It is unclear whether this reduction in cardiac hypertrophy resulted from direct effect on mechanisms governing muscle growth or is merely due to reduced afterload. The protein content as well as bladder weights and neuronal sizes in the OBS/P group were the same as obstructed rats receiving no drug, indicating changes in muscle and neuronal growth to be more closely associated with agents causing $Ca^{++}$ blockade rather than those affecting outlet resistance.

Following obstruction, an up-regulation of alpha adrenergic receptors occurs in the bladder. Therefore prazosin may alter voiding frequency though a direct effect on bladder smooth muscle. However, this alpha adrenergic blocker also acts centrally to inhibit micturition. Alternately, prazosin could prevent sympathetic-induced inhibition of bladder function. The lack of effect in normals, and the inhibition of urinary frequency in obstructed rats, is consistent with plasticity in reflex pathways supplying the hypertrophied bladder.

The instant disclosure ties $Ca^{++}$ with synchronous smooth muscle and neuronal growth in a central-peripheral effector system. The data illustrates that cytosolic $Ca^{++}$ is involved in cellular growth in response to mechanical stress. Furthermore, the foregoing reinforces that neuronal form can be altered by signals from the target organ.

EXAMPLE 7

Urine Tests in Humans

Figure 10:
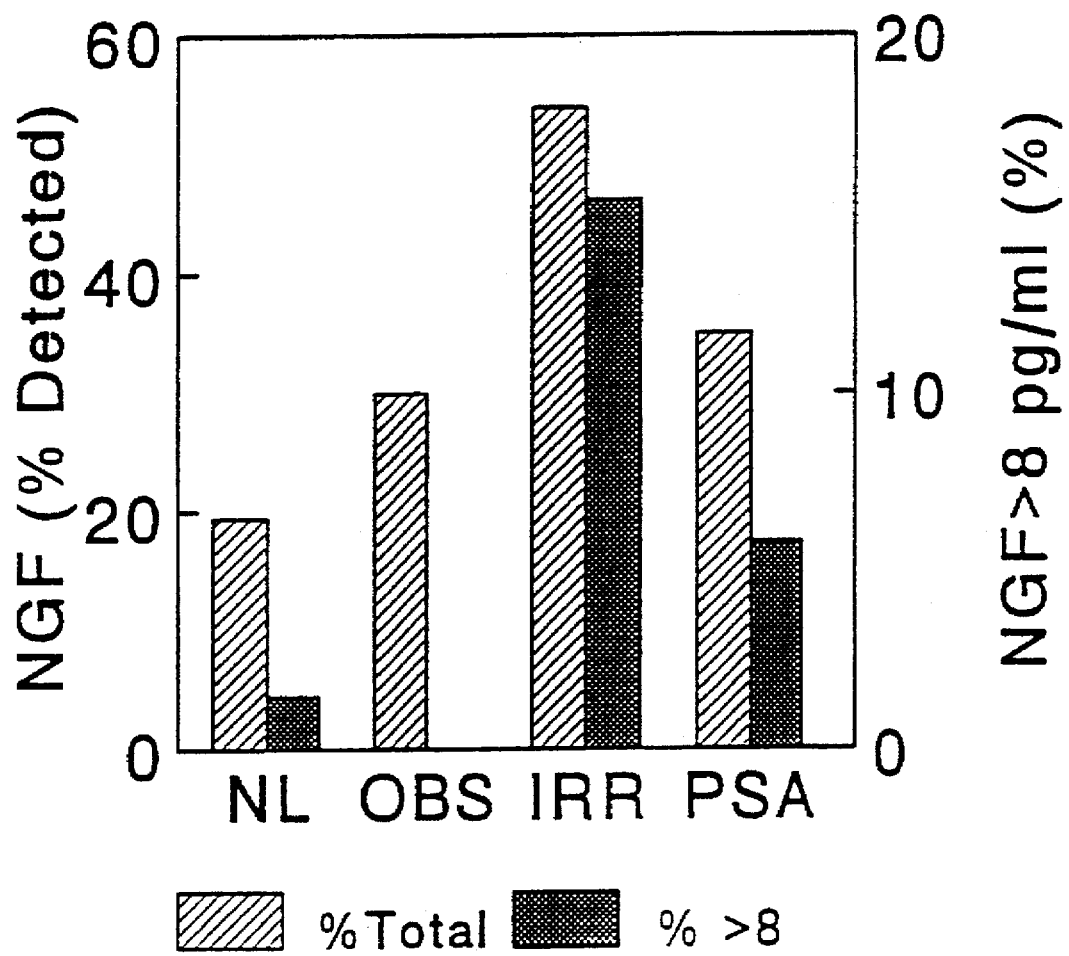
FIG. 10 is a graph illustrating the NGF in human urine.

The Department of Urology at the University of Virginia HSC sponsors a free prostate screening day each year. In 1992, 371 men underwent detailed history and examination for significant prostate disease and serum PSA deter-mined. Urine samples were also collected for assay of NGF (pg/ml) and protein and creatinine. Questionnaire data was used to assign each patient to one of four groups: Normal (318), obstructive symptoms (OBS: 10): Irritative and obstructive symptoms (IRR: 26) and asymptomatic with elevated PSA (PSA: 17). The data is graphed in FIG. 10, based on a percentage of the total in comparison to a total of those with NGF. The urine was assayed by a specific, two-site ELISA for NGF against a standard curve of recombinant human NGF (Genentech, Inc.). Minimum assay sensitivity was set at 3 times the standard deviation of the blank (0) NGF value, and was 2-3 pg/ml (0.1-0.15 pg NGF).

Using these analyses on the preliminary data, NGF in the urine as a test for irritative voiding symptoms in men over 50 has mediocre sensitivity (54%), but a fairly good specificity (81%). A high level of NGF (more than 8 pg/ml) has an excellent specificity (98.5%) but poor sensitivity. These data disclose that the patients with high levels of NGF in their urine are clustered specifically in the irritative voiding group, but that not all of the group have high NGF in the urine. The onset of symptoms is correlated with a rise in urine NGF, but in later stages, the urine values drop as the body becomes acclimated to the disease.

20-30% of symptomatic BPH patients have their symptoms spontaneously resolved after 6-12 months, indicating that the underlying pathogenesis of symptoms can take an uneven course. The results from animal experiments (See Example 8) support this possibility: at one week of obstruction, NGF in the urine has 75% sensitivity and 100% specificity.

Figure 11:
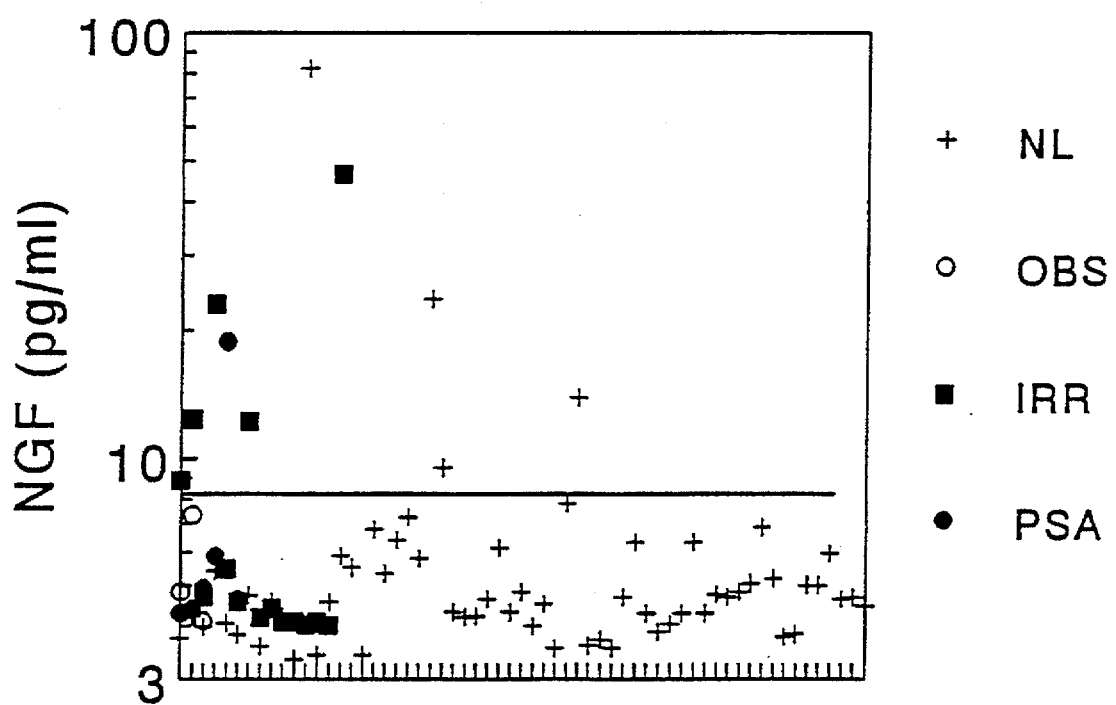
FIG. 11 is a graph as a scattergram on logarithmic scale showing the results of FIG. 10.

FIG. 11 presents all of the data for the four patient groups as a scattergram on a logarithmic scale. A line has been drawn at 8 pg/ml to indicate that patients with values above this level were invited back for an ultrasound study and to determine voiding flow rate. Note that 4 of 318 individuals of the normal group had these elevated NGF levels, along with 5 of 26 in the IRR group and 1 of 17 with an elevated PSA.

Figure 12:
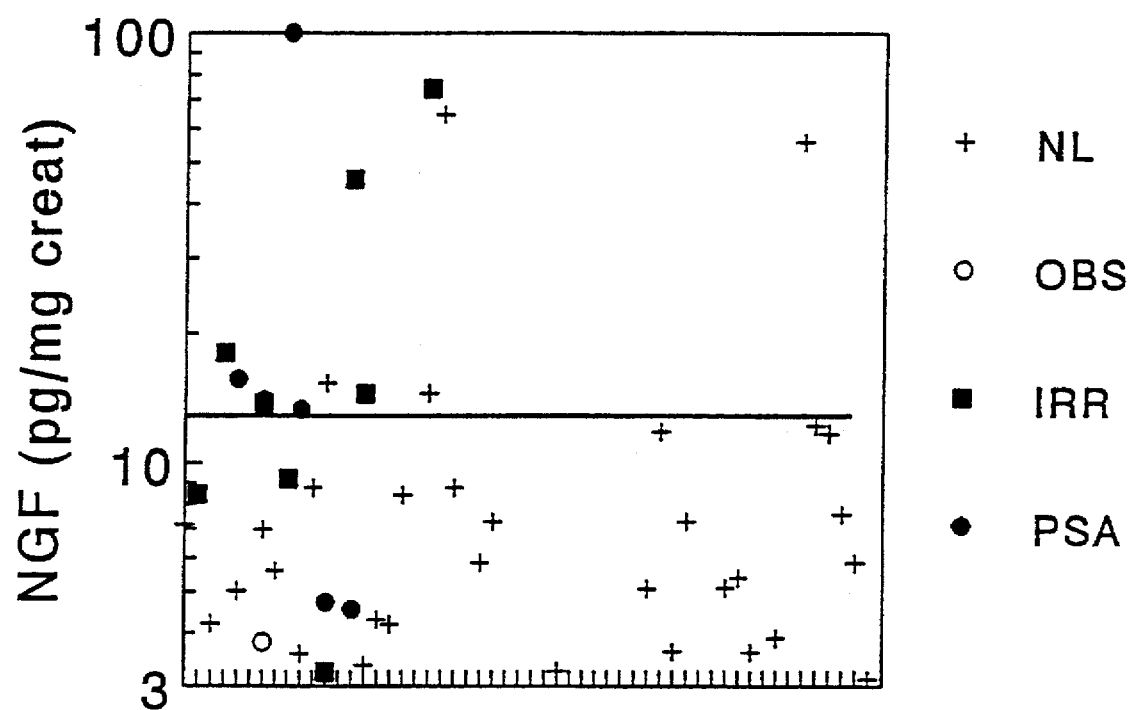
FIG. 12 shows the same data for those urines also assayed for urine creatinine levels and NGF expressed as pg NGF/ mg urine creatinine.

FIG. 12 shows the same data for those urines also assayed for urine creatinine levels and NGF expressed as pg NGF/mg urine creatinine. A line has been drawn at 13 pg/mg, segmenting the population as in FIG. 11. The distribution is comparable except for the PSA group. With NGF normalized to creatinine, three of the elevated PSA (but asymptomatic) individuals also display the high urine NGF. However, the urine samples from all but one of the same individuals in the IRR group and all of the normal group are above the line in both graphs. Thus, normalizing to creatinine brought 2 in the PSA group up, dropped 1 and raised 1 of the IRR individuals. The full data set on these few individuals is very indicative of the potential value of urine neurotrophin levels, as set forth in Table 3. One asymptomatic patient with a high level of NGF in the urine demonstrated a small (10 ml) post-void residual urine volume and a low urinary flow rate. The other asymptomatic individual had undergone vasectomy.

Four of the six were in the IRR group based upon the questionnaire data and the screening exam. Of these, two had substantial post-void residual volumes, one with low flow rate, one with reasonable flow rate, the examination indicating mild BPH. The other two patients in the IRR group were mildly symptomatic. One had a low voiding flow rate and the other a reasonable but not exceptional rate. Of the 4 "normal" individuals with >8 pg/ml NGF in the urine, two had previously undergone vasectomy, and the other two reported fathers with prostate cancer. It is possible that high rates of NGF in urine can indicate future medical problems.

The high NGF group contained two "mild" BPH cases with significant post-void volumes and one with a very low flow rate. Also, an apparently asymptomatic individual has a relatively low flow rate, residual urine and the highest level of NGF in the urine. One might predict that this person will begin to experience symptoms in the future.

EXAMPLE 8

Urine Tests in Animals

Urine was collected from rats during experiments on other projects, those involving experimental obstruction and normal controls. The results parallel that from the patients: 33% of normal rats have detectable levels of NGF in the urine taken as a 24-hour sample from a metabolic cage, with a mean concentration of 5.6±0.57 pg/ml (mean±SE). 75% of rats after one week of partial urethral ligation had detectable NGF, at 7.82±2.47 pg/ml, a higher level and increased incidence. All of these animals were female, indicating that the source of NGF in the urine of laboratory rats is not exclusively the prostate and testis. Thus, NGF in the urine in these obstructed animals may derive from the bladder and the urine level rises with the large increase in production during obstructive hypertrophy. Furthermore, kidneys in these animals were not hydronephrotic. Because 2.5S NGF, the smallest active form, is a dimer with a molecular weight approximately 26,000 daltons, it is unlikely that the protein is filtered by the kidney. NGF does not cross the blood-brain barrier unaided. However, the molecular form of NGF in the urine is not presently known. The two-site ELISA depends upon immunoreactivity and might measure a smaller protein fragment generated elsewhere and filtered and excreted by the kidney.

The increased incidence of detectable NGF and increased levels in the urine of obstructed female rats can relate to other, more general changes in the urine protein content. This was tested by SDS-PAGE analysis of urine from normal and rats obstructed for 1-3 weeks. The gel patterns, total protein content and creatinine content of the two groups were indistinguishable. These results illustrate that obstruction does not result in a wholesale shift in the spectrum of proteins in the urine but that the alterations are more subtle than can be detected by SDS-PAGE. The ELISA for NGF

TABLE 3

| | | Study Results - Individuals with >8 pg/ml Urine NGF | | | | |
|---|---|---|---|---|---|---|
| ID # | Symptom Group | NCF (pg/ml) | Mean/Peak VFR (ml/s) | PVR (cm³) | AUA Symptoms Score (I-PSS) | Dx (Exam. UltraS) |
| 201 | IRR | 12.25 | 2.8/4.7 | 180 | 13 | Slight BPH |
| 166 | IRR | 23.04 | 7.3/17.8 | 225 | ND | Mild trabeculae, Slight BPH |
| 335 | IRR | 46.45 | 2.6/6.2 | 0 | 13 | Normal |
| 50 | IRR | 8.9 | 7.3/14.6 | 0 | ND | Normal |
| 113 | N | 82.12 | 4.5/9.4 | 10 | 0 | Normal (Fam Hist:Pros Ca) |
| 145 | N | 23.07 | 11.4/22.3 | 0 | 0 | Normal (Vasectomy) | exceeds 2 orders of magnitude greater sensitivity than that of a western blot from SDS-PAGE gel.

Neurotrophic factor production participates in neural plasticity following outlet obstruction and inflammation because the neurons in the micturition pathways respond to the factors with growth and altered function. The cellular pathways responsible for regulating the synthesis and transfer of neurotrophic factors are activated and stimulated by the disease conditions. NGF and bFGF appear in the urine of patients with voiding dysfunction and in experimental animals with induced disease models. Therefore, the symptoms associated with BPH and IC that cause most patient concern and dictate physician intervention may be directly related to the production of these neurotrophic factors.

Not all attempts to use the presence of specific growth factors in the urine for diagnosis have been successful. One group of urine samples taken during a prostate cancer screening was collected and stored using a very different protocol. When assayed for levels of NGF, very few samples contained detectable NGF. No attempt was made to correlate the NGF levels in this group with specific clinical findings. However, efforts are in progress to optimize the handling of urine samples after collection and prior to analysis to ensure that factors are not degraded or lost to detection. An entirely different approach was also taken. Urine samples from rat disease models and human samples were analyzed by polyacrylamide gel electrophoresis under denaturing (SDS) conditions (SDS-PAGE). This separates urine proteins based upon differential rate of migration through an acrylamide gel in response to an applied electric field, a separation method based roughly upon protein size. The gels were transferred to a membrane support and immuno-probed with antibodies against the factors of interest (Western blot). This detection method was not sensitive enough to detect or measure the urine neurotrophic factors.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A method of treating hyperactive voiding associated with excessive nerve growth factor production and nerve growth in a patient in need thereof comprising administering to said patient a $Ca^{++}$ channel blocker.

2. The method according to claim 1 wherein said $ca^{++}$ channel blocker is verapamil.

3. The method according to claim 1 wherein said $Ca^{++}$ channel blocker is diltiazem.

4. The method according to claim 1 wherein said hyperactive voiding is associated with benign prostatic hyperplasia.

5. The method according to claim 1 wherein said hyperactive voiding is associated with interstitial cystitis.

6. The method according to claim 1 wherein said $Ca^{++}$ blocker is administered systemically.

* * * * *